(12) United States Patent
Faulhaber

(10) Patent No.: US 12,029,659 B2
(45) Date of Patent: *Jul. 9, 2024

(54) STABILIZED INTERVERTEBRAL SPACER

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/563,470

(22) Filed: Dec. 28, 2021

(65) Prior Publication Data

US 2022/0117750 A1     Apr. 21, 2022

Related U.S. Application Data

(63) Continuation of application No. 16/704,643, filed on Dec. 5, 2019, now Pat. No. 11,259,938, which is a continuation of application No. 15/613,710, filed on Jun. 5, 2017, now Pat. No. 10,524,928, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4455* (2013.01); *A61F 2/4611* (2013.01); *A61F 2002/30405* (2013.01); *A61F 2002/30482* (2013.01); *A61F 2002/30507* (2013.01); *A61F 2002/30515* (2013.01); *A61F 2002/30538* (2013.01); *A61F 2002/30579* (2013.01); *A61F 2002/30593* (2013.01); *A61F 2002/30836* (2013.01); *A61F 2002/30841* (2013.01); *A61F 2/4603* (2013.01); *A61F 2002/4627* (2013.01);
(Continued)

(58) Field of Classification Search
CPC ...... A61F 2/4425; A61F 2/4455; A61F 2/447; A61F 2002/443
See application file for complete search history.

(56) References Cited

U.S. PATENT DOCUMENTS

| 4,349,921 A | 9/1982 | Kuntz |
| 4,599,086 A | 7/1986 | Doty |
| 4,863,476 A | 9/1989 | Shepperd |

(Continued)

FOREIGN PATENT DOCUMENTS

| CA | 2088066 A1 | 1/1992 |
| DE | 4012622 C1 | 7/1991 |

(Continued)

*Primary Examiner* — Anu Ramana

(57) ABSTRACT

A spacer for separating bones of a joint, the spacer includes a first endplate configured to engage a first bone of the joint; a second endplate configured to engage a second bone of the joint; tissue engaging projections, wherein the tissue engaging projections are moveable from a retracted position to a deployed position; and an actuation subassembly that extends between the first endplate and the second endplate, wherein the actuation subassembly comprise a drive nut, a drive screw coupled to the drive nut, and a cam frame coupled to the drive screw, wherein the cam frame is disposed between the first endplate and the second endplate to engage the tissue engaging projections.

18 Claims, 24 Drawing Sheets

Related U.S. Application Data continuation-in-part of application No. 14/969,376, filed on Dec. 15, 2015, now abandoned.

(52) U.S. Cl.
CPC .............. *A61F 2310/00023* (2013.01); *A61F 2310/00029* (2013.01); *A61F 2310/00407* (2013.01)

(56) References Cited

U.S. PATENT DOCUMENTS

| | | | |
|---|---|---|---|
| 4,863,477 | A | 9/1989 | Monson |
| 5,123,926 | A | 6/1992 | Pisharodi |
| 5,290,312 | A | 3/1994 | Kojimoto et al. |
| 5,306,310 | A | 4/1994 | Siebels |
| 5,375,823 | A | 12/1994 | Navas |
| 5,390,683 | A | 2/1995 | Pisharodi |
| 5,522,899 | A | 6/1996 | Michelson |
| 5,534,030 | A | 7/1996 | Navarro et al. |
| 5,554,191 | A | 9/1996 | Lahille et al. |
| 5,571,192 | A | 11/1996 | Schonhoffer |
| 5,645,596 | A | 7/1997 | Kim |
| 5,653,763 | A | 8/1997 | Errico et al. |
| 5,665,122 | A | 9/1997 | Kambin |
| 5,676,701 | A | 10/1997 | Yuan et al. |
| 5,800,547 | A * | 9/1998 | Schafer ............... A61F 2/442 623/17.16 |
| 6,039,761 | A | 3/2000 | Li et al. |
| 6,045,579 | A | 4/2000 | Hochschuler et al. |
| 6,080,193 | A | 6/2000 | Hochschuler et al. |
| 6,099,531 | A | 8/2000 | Bonutti |
| 6,126,689 | A | 10/2000 | Brett |
| 6,176,882 | B1 | 1/2001 | Biedermann et al. |
| 6,258,125 | B1 | 7/2001 | Paul et al. |
| 6,527,803 | B1 * | 3/2003 | Crozet ............... A61F 2/442 606/31 |
| 6,558,423 | B1 | 5/2003 | Michelson |
| 6,562,074 | B2 | 5/2003 | Gerbec et al. |
| 6,576,016 | B1 | 6/2003 | Hochschuler et al. |
| 6,554,863 | B2 | 8/2003 | Paul et al. |
| 6,641,614 | B1 | 11/2003 | Wagner et al. |
| 6,648,917 | B2 | 11/2003 | Gerbec et al. |
| 6,666,891 | B2 | 12/2003 | Boehm, Jr. et al. |
| 6,692,495 | B1 | 2/2004 | Zacouto |
| 6,706,070 | B1 | 3/2004 | Wagner et al. |
| 6,752,832 | B2 | 6/2004 | Ulrich |
| 6,814,756 | B1 | 11/2004 | Michelson |
| 6,830,589 | B2 | 12/2004 | Erickson |
| 6,849,093 | B2 | 2/2005 | Michelson |
| 6,852,129 | B2 | 2/2005 | Gerbec et al. |
| 6,863,673 | B2 | 3/2005 | Gerbec et al. |
| 6,881,228 | B2 | 4/2005 | Zdeblick et al. |
| 7,018,415 | B1 | 3/2006 | McKay |
| 7,070,598 | B2 | 7/2006 | Lim et al. |
| 7,204,853 | B2 | 4/2007 | Gordon |
| 7,217,291 | B2 | 5/2007 | Zucherman et al. |
| 7,282,063 | B2 | 10/2007 | Cohen et al. |
| 7,316,714 | B2 | 1/2008 | Gordon |
| 7,473,276 | B2 | 1/2009 | Aebi et al. |
| 7,547,325 | B2 | 6/2009 | Biedermann et al. |
| 7,621,953 | B2 | 11/2009 | Braddock, Jr. et al. |
| 7,641,693 | B2 | 1/2010 | Gutlin et al. |
| 7,682,396 | B2 | 3/2010 | Beaurain et al. |
| 7,749,270 | B2 | 7/2010 | Peterman |
| 7,753,958 | B2 | 7/2010 | Gordon |
| 7,771,473 | B2 | 8/2010 | Thramann |
| 7,780,732 | B2 | 8/2010 | Abernathie |
| 7,799,081 | B2 | 9/2010 | McKinley |
| 7,815,683 | B2 | 10/2010 | Melkent et al. |
| 7,837,734 | B2 | 11/2010 | Zucherman et al. |
| 7,875,078 | B2 | 1/2011 | Wysocki et al. |
| 7,901,409 | B2 | 3/2011 | Canaveral et al. |
| 7,909,869 | B2 | 3/2011 | Gordon |
| 7,951,199 | B2 | 5/2011 | Miller |
| 7,985,256 | B2 | 7/2011 | Grotz et al. |
| 8,062,375 | B2 | 11/2011 | Glerum |
| 8,070,813 | B2 | 12/2011 | Grotz et al. |
| 8,123,810 | B2 | 2/2012 | Gordon |
| 8,137,405 | B2 | 3/2012 | Kostuik et al. |
| 8,192,495 | B2 | 6/2012 | Simpson et al. |
| 8,303,663 | B2 | 11/2012 | Jimenez et al. |
| 8,377,140 | B2 | 2/2013 | DeFalco et al. |
| 8,394,129 | B2 | 3/2013 | Lopez et al. |
| 8,394,143 | B2 | 3/2013 | Grotz et al. |
| 8,435,296 | B2 | 5/2013 | Kadaba et al. |
| 8,454,695 | B2 | 6/2013 | Grotz et al. |
| 8,647,386 | B2 | 2/2014 | Gordon |
| 8,696,751 | B2 | 4/2014 | Ashley et al. |
| 8,715,350 | B2 * | 5/2014 | Janowski ............... A61F 2/4611 623/17.14 |
| 8,771,360 | B2 | 7/2014 | Jimenez et al. |
| 8,894,710 | B2 | 11/2014 | Simpson et al. |
| 8,932,355 | B2 | 1/2015 | Grotz et al. |
| 8,940,049 | B1 | 1/2015 | Jlmenez et al. |
| 8,956,413 | B2 | 2/2015 | Ashley et al. |
| 8,992,620 | B2 | 3/2015 | Ashley et al. |
| 9,028,550 | B2 | 5/2015 | Shulock et al. |
| 9,358,125 | B2 | 6/2016 | Jlmenez et al. |
| 9,532,883 | B2 | 1/2017 | McLuen et al. |
| 9,622,878 | B2 | 4/2017 | Grotz |
| 10,105,240 | B2 * | 10/2018 | DeFelice ............... A61F 2/44 |
| 2002/0045945 | A1 | 4/2002 | Liu |
| 2002/0068976 | A1 | 6/2002 | Jackson |
| 2002/0068977 | A1 | 6/2002 | Jackson |
| 2003/0176925 | A1 | 9/2003 | Boehm et al. |
| 2004/0030387 | A1 | 2/2004 | Landry et al. |
| 2004/0049271 | A1 | 3/2004 | Biedermann |
| 2004/0054412 | A1 | 3/2004 | Gerbec et al. |
| 2004/0087947 | A1 | 5/2004 | Lim et al. |
| 2004/0153065 | A1 | 8/2004 | Lim |
| 2005/0021041 | A1 | 1/2005 | Michelson |
| 2005/0021145 | A1 | 1/2005 | de Villiers et al. |
| 2005/0033432 | A1 | 2/2005 | Gordon |
| 2005/0080422 | A1 | 4/2005 | Otte et al. |
| 2005/0113916 | A1 | 5/2005 | Branch |
| 2005/0149188 | A1 | 7/2005 | Cook |
| 2005/0171541 | A1 | 8/2005 | Boehm |
| 2005/0251258 | A1 | 11/2005 | Jackson |
| 2005/0273171 | A1 | 12/2005 | Gordon |
| 2005/0273174 | A1 | 12/2005 | Gordon |
| 2005/0278026 | A1 | 12/2005 | Gordon |
| 2005/0283244 | A1 | 12/2005 | Gordon |
| 2005/0283245 | A1 | 12/2005 | Gordon |
| 2006/0004453 | A1 | 1/2006 | Bartish, Jr. et al. |
| 2006/0015184 | A1 | 1/2006 | Winterbottom et al. |
| 2006/0058878 | A1 | 3/2006 | Michelson |
| 2006/0084986 | A1 | 4/2006 | Grinberg et al. |
| 2006/0095136 | A1 | 5/2006 | McLuen |
| 2006/0122701 | A1 | 6/2006 | Kister |
| 2006/0129244 | A1 | 6/2006 | Ensign |
| 2006/0142859 | A1 | 6/2006 | Mcluen |
| 2006/0149385 | A1 | 7/2006 | Mckay |
| 2006/0195192 | A1 | 8/2006 | Gordon et al. |
| 2006/0229729 | A1 | 10/2006 | Gordon |
| 2006/0241770 | A1 | 10/2006 | Rhoda et al. |
| 2006/0253201 | A1 | 11/2006 | Mcluen |
| 2007/0043442 | A1 | 2/2007 | Abernathie |
| 2007/0050030 | A1 | 3/2007 | Kim |
| 2007/0050032 | A1 | 3/2007 | Gittings et al. |
| 2007/0055377 | A1 | 3/2007 | Hanson et al. |
| 2007/0191951 | A1 | 8/2007 | Branch |
| 2007/0255415 | A1 | 11/2007 | Edie et al. |
| 2007/0270963 | A1 | 11/2007 | Melkent et al. |
| 2007/0270968 | A1 | 11/2007 | Baynham |
| 2008/0021559 | A1 | 1/2008 | Thramann |
| 2008/0065222 | A1 | 3/2008 | Hamada |
| 2008/0114467 | A1 | 5/2008 | Capote et al. |
| 2008/0140207 | A1 | 6/2008 | Olmos et al. |
| 2008/0147194 | A1 | 6/2008 | Grotz et al. |
| 2008/0161933 | A1 | 7/2008 | Grotz et al. |
| 2008/0167657 | A1 | 7/2008 | Greenhalgh |
| 2008/0183204 | A1 | 7/2008 | Greenhalgh et al. |
| 2008/0221694 | A1 | 9/2008 | Warnick et al. |
| 2008/0275455 | A1 | 11/2008 | Berry et al. |

(56) References Cited

U.S. PATENT DOCUMENTS

| | | |
|---|---|---|
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0164020 A1* | 6/2009 | Janowski ............... A61F 2/4465 606/247 |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1* | 1/2013 | Glerum ............... A61F 2/447 623/17.16 |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

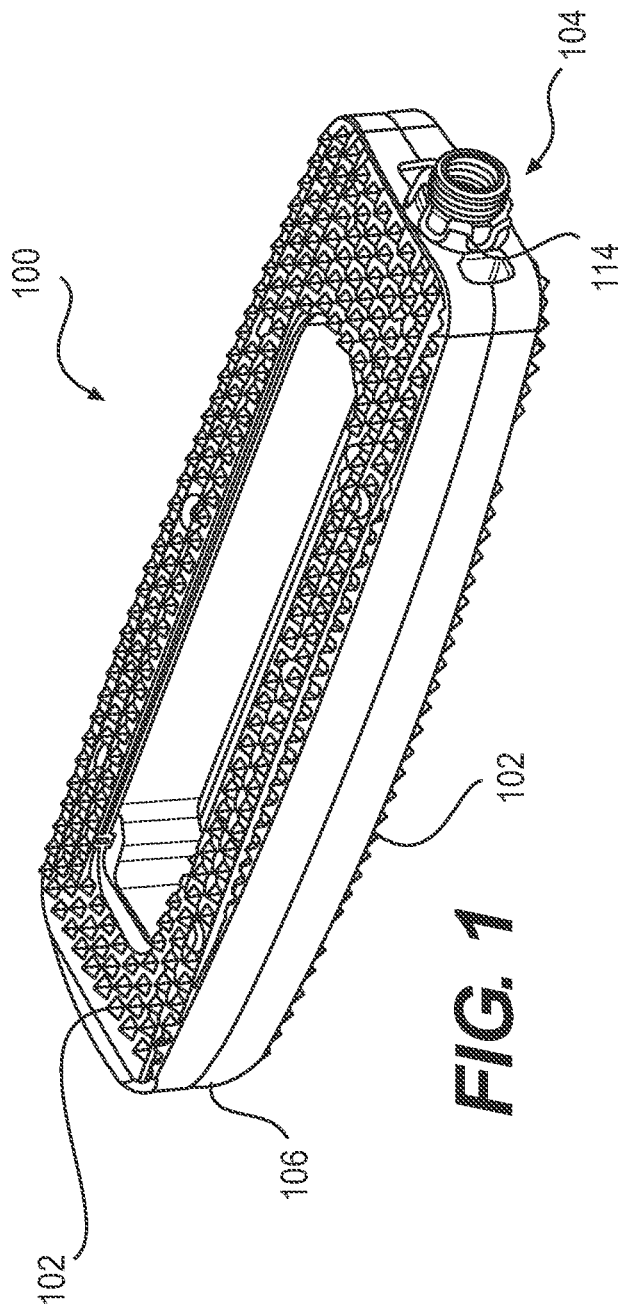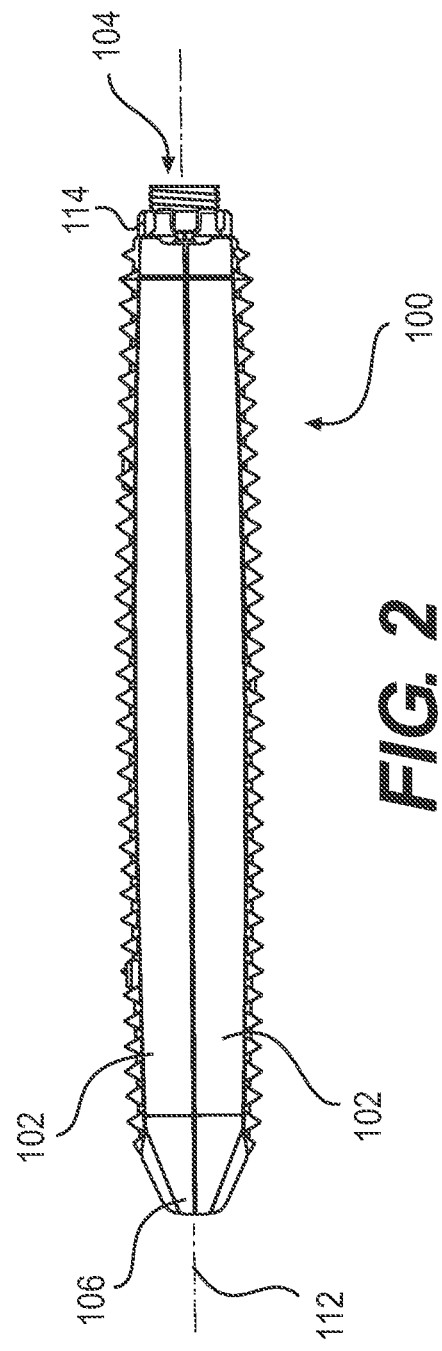

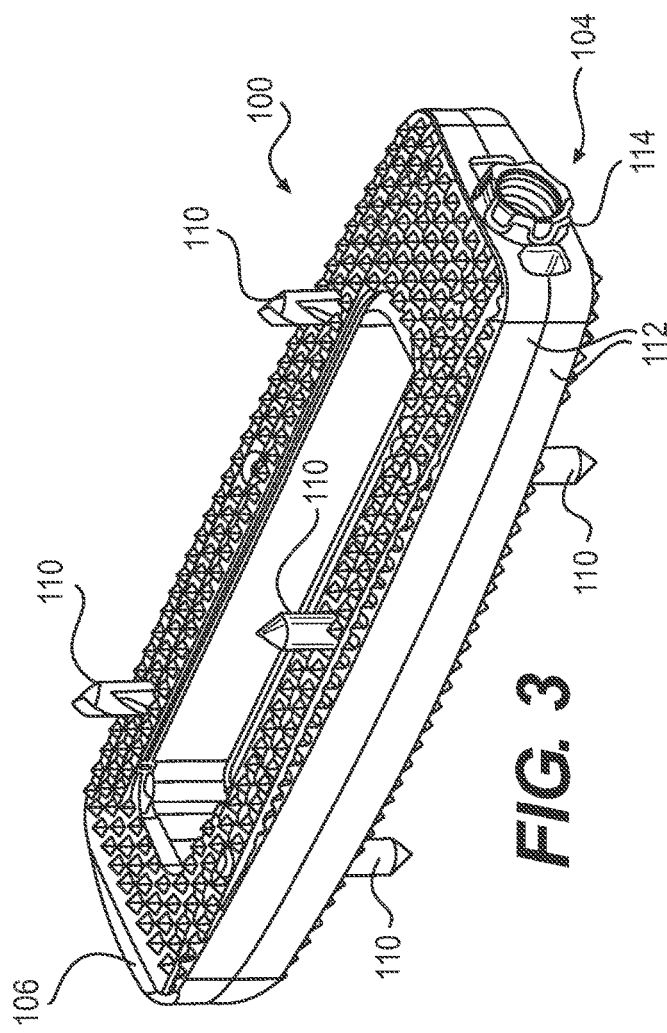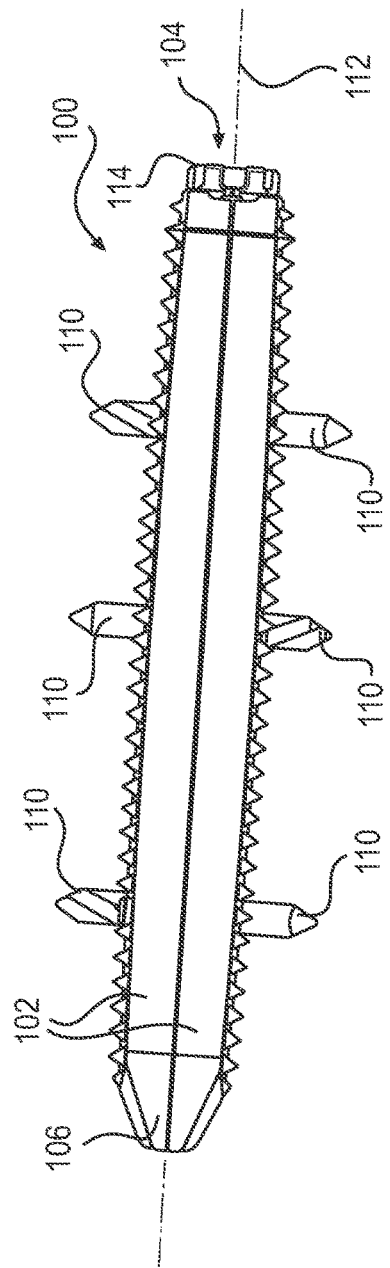
FIG. 3
FIG. 4

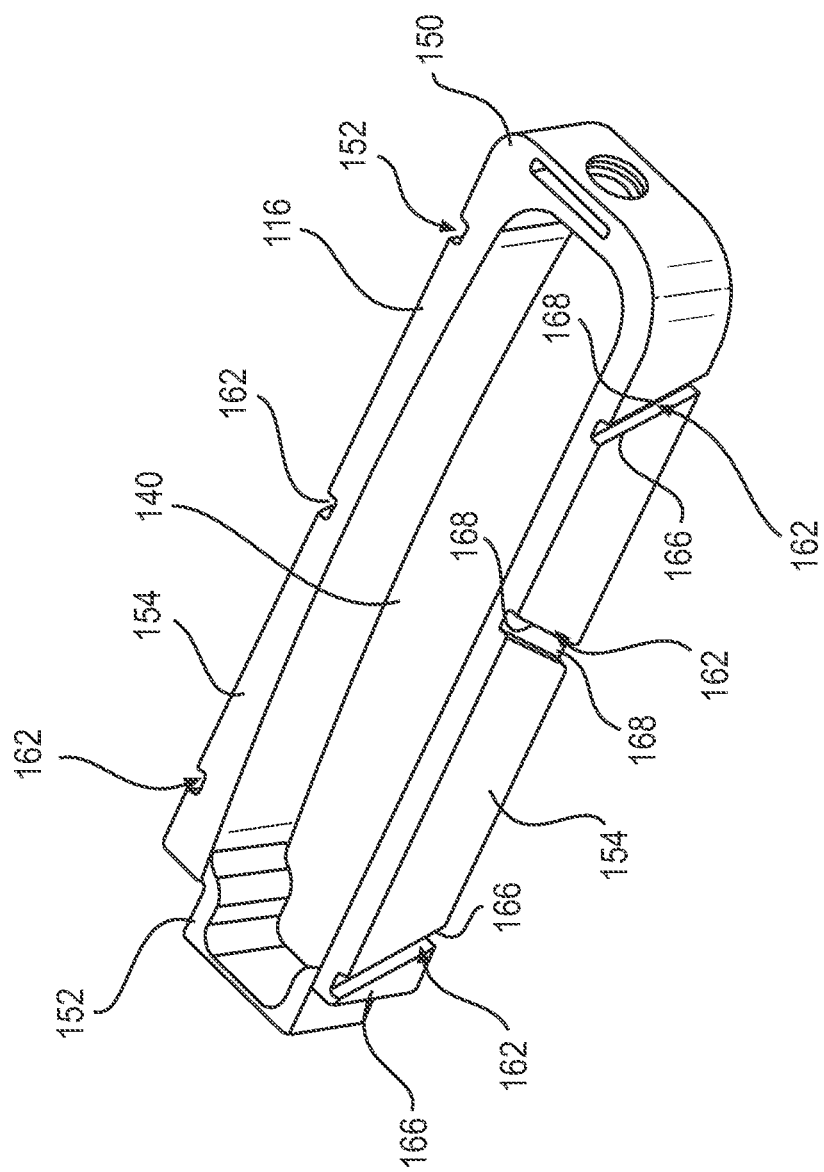

STABILIZED INTERVERTEBRAL SPACER

CROSS REFERENCE TO RELATED APPLICATION

This application is a continuation of U.S. patent application Ser. No. 16/704,643, filed Dec. 5, 2019 (published as U.S. Pat. Pub. No. 2020-0107938), which is a continuation of U.S. patent application Ser. No. 15/613,710, filed on Jun. 5, 2017 (now U.S. Pat. No. 10,524,928), which is a continuation-in-part of U.S. patent application Ser. No. 14/969,376, filed Dec. 15, 2015 (abandoned), which is hereby incorporated by reference in its entirety for all purposes.

FIELD OF THE INVENTION

This invention relates to stabilizing adjacent vertebrae of the spine by inserting an intervertebral spacer, and more particularly an intervertebral spacer that is stabilized.

BACKGROUND

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan n the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY

In accordance with an embodiment of the disclosure, a spacer for separating bone of a joint may be provided. The spacer may comprise a first endplate configured to engage a first bone of the joint. The spacer may further comprise a second endplate configured to engage a second bone of the joint. The spacer may further comprise tissue engaging projections, wherein the tissue engaging projections are moveable from a retracted position to a deployed position. The spacer may further comprise an actuation subassembly that extends between the first endplate and the second endplate, wherein the actuation subassembly comprise a drive nut, a drive screw coupled to the drive nut, and a cam frame coupled to the drive screw, wherein the cam frame is disposed between the first endplate and the second endplate to engage the tissue engaging projections.

In accordance with an embodiment of the disclosure, a method of separating bones of a joint may be provided. The method may comprise inserting a spacer between bones of the joint. The method may further comprise translating a cam frame along a longitudinal axis of the spacer, wherein tissue engaging projections ride along cam slots formed in lateral sides of the cam frame such that translation of the cam frame drives the tissue engaging projections to extend from endplates of the spacer and engage the bones of the joint.

BRIEF DESCRIPTION OF THE DRAWINGS

These drawings illustrate certain aspects of some examples of the present invention, and should not be used to limit or define the invention.

FIG. 1 is a perspective view of a spacer in a retracted position in accordance with example embodiments;

FIG. 2 is a side view of a spacer in a retracted position in accordance with example embodiments;

FIG. 3 is a perspective view of a spacer with body tissue engaging projections deployed in accordance with example embodiments;

FIG. 4 is a side view of a spacer with body tissue engaging projections deployed in accordance with example embodiments;

FIG. 7 illustrates a cam frame of a spacer of in accordance with example embodiments;

DETAILED DESCRIPTION

Figure 5:
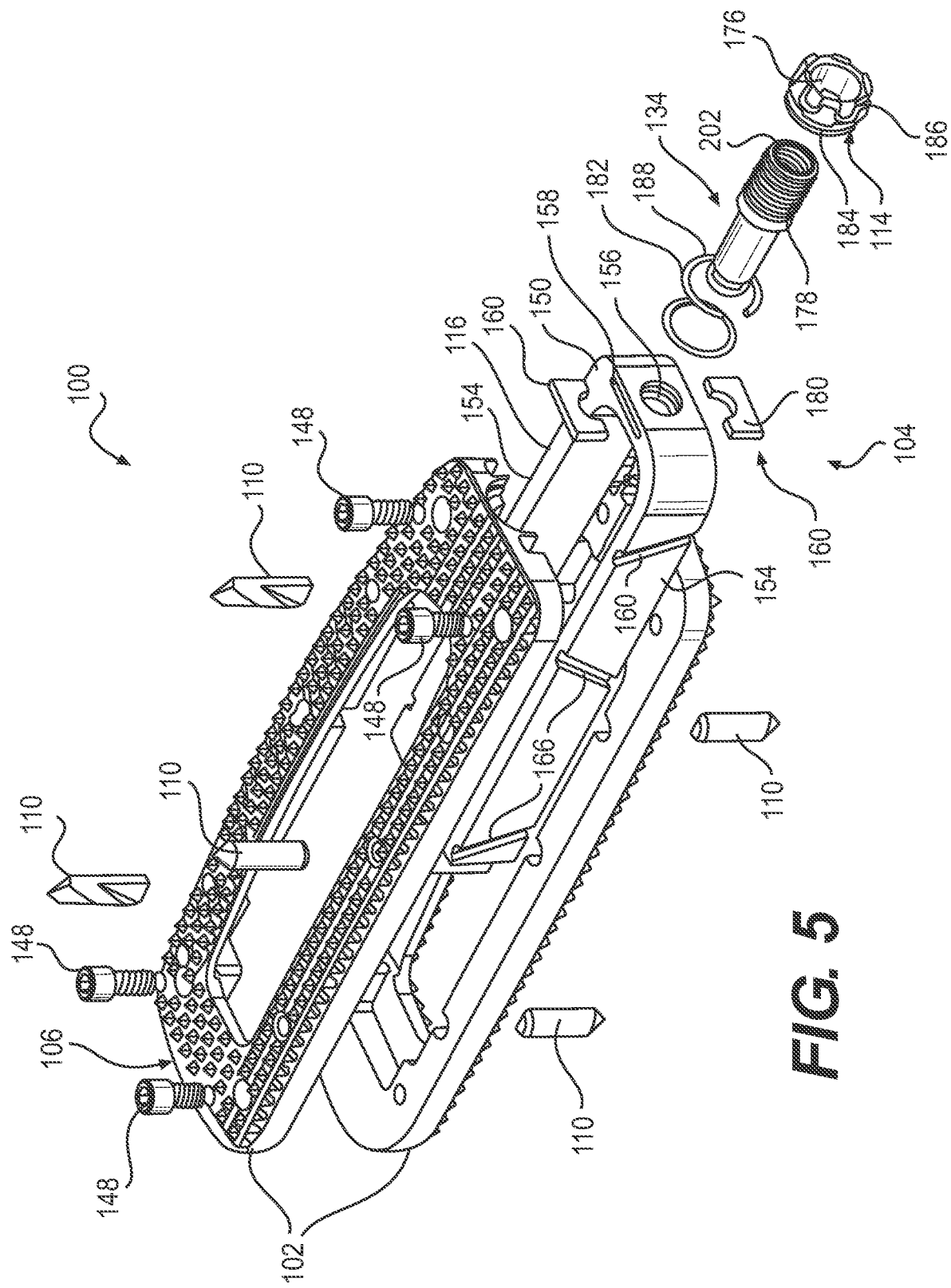
FIG. 5 is an exploded view of a spacer in accordance with example embodiments.

Embodiments are directed to a spacer that may be inserted between two adjacent bony surfaces to promote the fusion of bony surfaces. After insertion, the spacer may be stabilized by deployment of body tissue engaging projections which may engage adjacent body tissue to prevent migration and/or tipping of the spacer prior to fusion occurring. Although intended to be useful with any adjacent bony surface in which fusion is desired, the spacer may advantageously be applied to insertion between two adjacent vertebral bodies in any section of the spine, including the cervical, thoracic, lumbar, and sacral vertebral sections. More than one spacer may be implanted within the body, for example between successive or separated vertebrae, between adjacent vertebrae. The use of multiple spacers is particularly advantageous for patients whose back pain is not limited to a localized area, or for patients whose localized damage has progressed to other areas of the spine.

The spacer and methods for its insertion can be used in a treatment protocol for any of a wide variety of conditions in a patient involving diseased or damaged bony structures. The patient can be a human being. Additionally, it is contemplated that the spacer may be useful in veterinary science for any animal having adjacent bony structures to be fused. Body tissue engaging projections may be retracted during insertion of spacer. After the spacer has been inserted, body tissue engaging projections may be deployed, for example. Although the spacer is exemplified herein for use in the spine, the spacer is contemplated for fusion of any bony structures. While the spacers are described herein using several varying embodiments, the spacers are not limited to these embodiments. An element of one embodiment may be used in another embodiment, or an embodiment may not include all described elements.

With reference now to FIGS. 1-5, embodiments of spacer 100 may comprise endplates 102 and actuation subassembly 104. In the embodiment shown, endplates 102 may be generally symmetrical, and spacer 100 can be implanted with either endplate 102 positioned superior with respect to the other. In other embodiments, they may be dissimilar, and a particular orientation may then be advantageous or necessary.

Spacer 100 forms a distal end 106 which may be inserted first into the body, and which can be tapered to facilitate insertion between body tissues. Spacer 100 also forms a proximal end 108, to which a spacer insertion device (e.g. 190 shown on FIGS. 12a and 12b) may be connected. Spacer 100 may be inserted in a retracted position, as shown on FIGS. 1 and 2. In the retracted position, body tissue engaging projections 110 (best seen on FIG. 5) may be disposed within spacer 100 and may not extend beyond endplates 102. In other words, body tissue engaging projections 110 may be considered to be in a retracted position. A spacer longitudinal axis 112 (best seen on FIGS. 2 and 4) may be defined between distal end 106 and proximal end 108. After insertion of the spacer 100, the body tissue engaging projections 110 may be deployed to engage tissue (e.g., vertebral bodies), for example, to fixate the spacer 100 in place. FIGS. 3 and 4 illustrate spacer 100 with body tissue engaging projections 110 in a deployed position. To deploy body tissue engaging projections 110, drive nut 114 may be rotated causing advancement and/or retraction of cam frame 116 along spacer longitudinal axis 112. As the cam frame 116 (best seen on FIG. 5) is moved, it engages body tissue engaging projections 110 driving them outward such that the body tissue engaging projections 110 are deployed through the endplates 102.

Figure 6B:
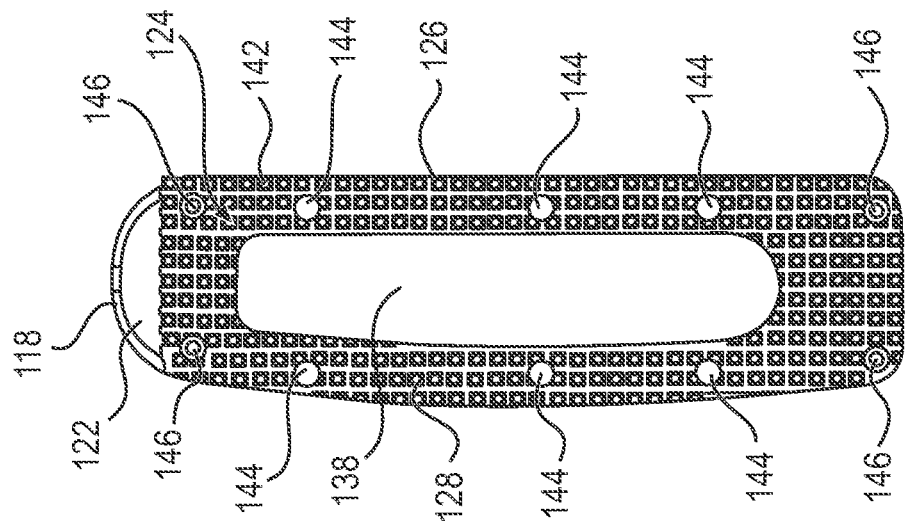
FIGS. 6a and 6b illustrate an endplate of a spacer in accordance example embodiments.
Figure 6A:
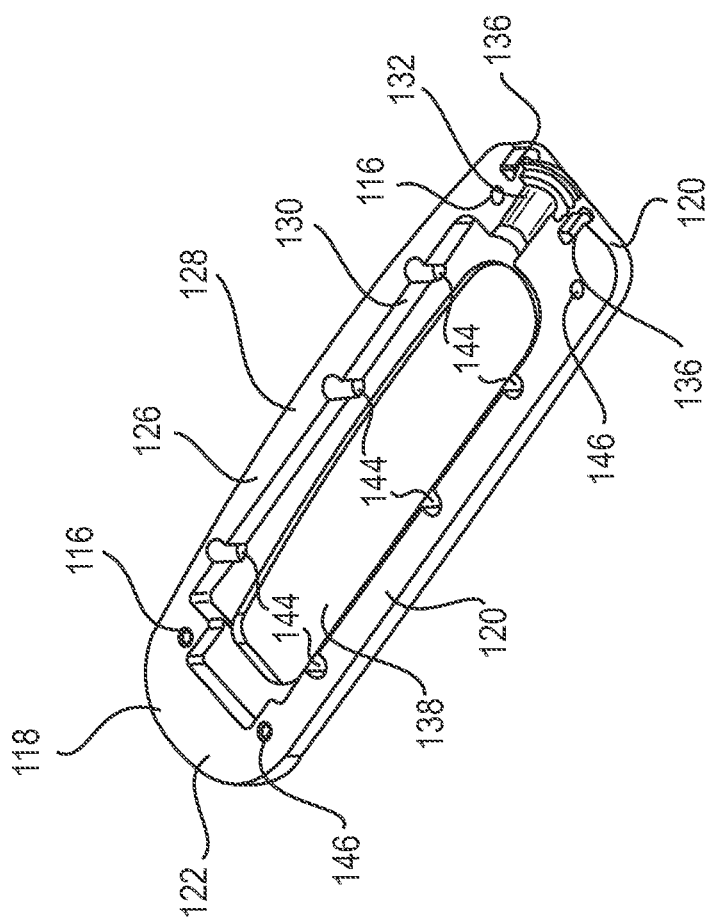

Turning now to FIGS. 6a and 6b, embodiments of endplates 102 will now be described. It should be understood that the endplates 102 may be symmetrical so the description may equally apply to either of endplates 102. Endplates 102 may have a proximal end 118 and a distal end 120. Nose 122 at distal end 120 may be tapered or otherwise formed to facilitate insertion into a desired location. As best seen on FIG. 6b, endplates 102 may further comprise an outer facing surface 124 connecting proximal end 118 and distal end 120. As illustrated, endplates 102 may also comprise lateral sides 126. Endplates 102 may further comprise an inner facing surface 128. Inner facing surface 128 may have a recessed portion 130 in which cam frame 116 may be received. In the illustrated embodiment, endplates 102 may further comprise a cutout 132 for receiving drive screw 134 (e.g., shown on FIG. 5). Endplates 102 may further comprise an insertion tool engagement 136 that engages a corresponding engagement of spacer insertion device (e.g., 190 on FIGS. 12a and 12b).

In some embodiments, endplates 102 may further comprise through openings 138. Through openings 138 may form an opening in endplates 102 that extends from outer facing surface 124 to inner facing surface 128. The through opening 138, in an exemplary embodiment, may be sized to receive bone graft or similar bone growth inducing material and further allow the bone graft or similar bone growth inducing material to be packed in a central opening 140 in cam frame 116 (best seen on FIG. 7).

With specific reference to FIG. 6b, the outer facing surfaces 124 of endplates 102 may be flat and generally planar to allow the outer facing surfaces 124 to engage with the adjacent tissue (e.g., vertebral body). Alternatively, not shown, the outer facing surfaces 124 may be curved, convexly or concavely to allow, for a greater or lesser degree of engagement with the adjacent tissue. It is also contemplated that the outer facing surfaces 124 can be generally planar but include a generally straight ramped surface or a curved ramped surface. Where present, the ramped surface may allow for engagement with the adjacent tissue in a lordotic fashion. In the illustrated embodiment, the outer facing surfaces 124 comprises texturing 142, for example, to aid in gripping the adjacent tissue. Although not limited to the following, the texturing can include teeth, ridges, friction increasing elements, keels, or gripping or purchasing projections.

As seen in FIGS. 6a and 6b, the endplates 102 may further include a plurality of holes 144. Depending on the particular endplate 102, certain of the holes 144 may be blind holes if desired. In the holes 144, the body tissue engaging projections 110 may be disposed. When deployed, the body tissue engaging projections 110 may be deployed so that they project beyond the outer facing surfaces 124 of the endplates 102. As illustrated, the holes 144 may be arranged in a row in each lateral side 126 of the endplates 102. In the illustrated embodiment, there are three holes 144 in each lateral side 126. However, it should be understood that the number and arrangement of holes 144 in endplates 102 may be selected as desired for a particular application. In addition, fastener holes 146 may be also be disposed in at least one of the endplates 102. Fasteners 148 (e.g., shown on FIG. 5) may be disposed in fastener holes 146 to secure the endplates 102 to one another.

Endplates 102 may additionally, or alternatively, be resilient, so that they may conform to bony surfaces, forming a more stable support platform. Accordingly, endplates 102 can be fabricated from a polymeric material, a naturally resilient material, or a resilient metal, for example a shape memory alloy, or any other resilient biocompatible material of sufficient strength and durability for separating bones within the body.

Turning now to FIGS. 5 and 7, cam frame 116 will now be described in more detail with respect to particular embodiments. As illustrated, cam frame 116 may comprise proximal frame end 150, distal frame end 152, and lateral frame sides 154. Lateral frame sides may extend from proximal frame end 150 to distal frame end 152. Proximal frame end 150, distal frame end 152, and lateral frame sides 154 may define central opening 140 in cam frame 116. Opening 156 may be formed in proximal frame end 150 through which drive screw 134 may be disposed. Retaining slots 158 may be formed in proximal frame end 150 that intersects opening 156. One or more screw retaining plates 160 may be inserted into retaining slots 158 to retain drive screw 134.

In some embodiments, cam slots 162 may be formed in lateral frame sides 154. As illustrated three cam slots 162 may be formed in each of lateral frame sides 154. However, it should be understood that more or less than three cam slots 162 may be used. The number of cam slots 162 generally may correspond to the number of body tissue engaging projections 110. At least a portion of body tissue engaging projections 110 may be disposed in a corresponding one of cam slots 162. By way of example, each of body tissue engaging projections 110 may include a protuberance, such as ridge 164 (best seen on FIGS. 8 and 9). The ridge 164 may ride in cam slots 162. The cam slots 162 may include drive surfaces 166 that engage body tissue engaging projections 110. The cam slots 162 may operate to change the direction of the linear movement of cam frame 116. For example, movement of the cam frame 116 along the spacer longitudinal axis 112 may be changed to movement of body tissue engaging projections 110 in a direction generally transverse to spacer longitudinal axis 112. As the cam frame 116 is moved, for example, along the spacer longitudinal axis 112, the cam slots 162 may engage the body tissue engaging projections 110 to drive the body tissue engaging projections 110 into their deployed position. In the deployed position, a first position of the body tissue engaging projections 110 may extend through one of the endplates 102, while a second portion of the body tissue engaging projections 110 may extend through another of the endplates 102. Movement of the cam frame 116 in the opposite direction may cause the cam slots 162 to engage the body tissue engaging projections 110 to drive the body tissue engaging projections 110 into a retracted position. As illustrated, the cam slots 162 may be angled with respect to spacer longitudinal axis 112. As will be appreciated, the angle of cam slots 162 may be adjusted to modify how far the body tissue engaging projections 110 may project from spacer 100.

Figure 9:
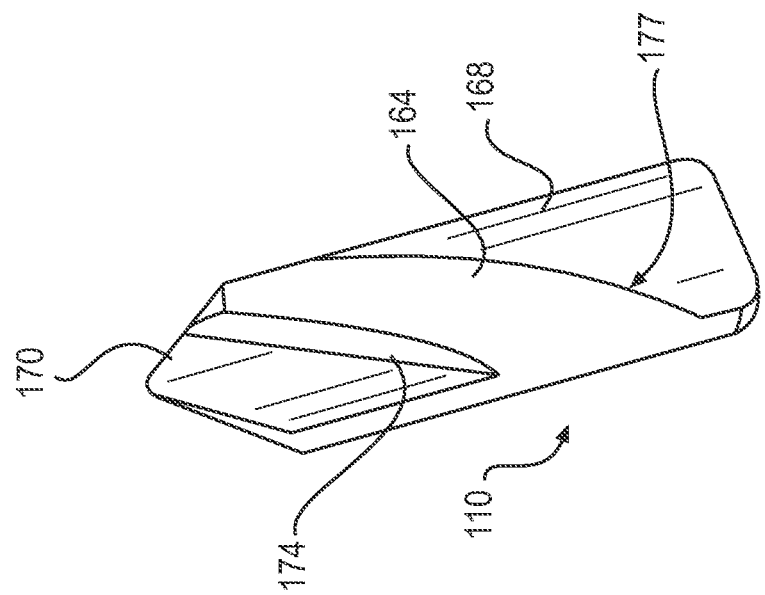
FIGS. 8 and 9 illustrate body tissue engaging projections in accordance with example embodiments.
Figure 8:
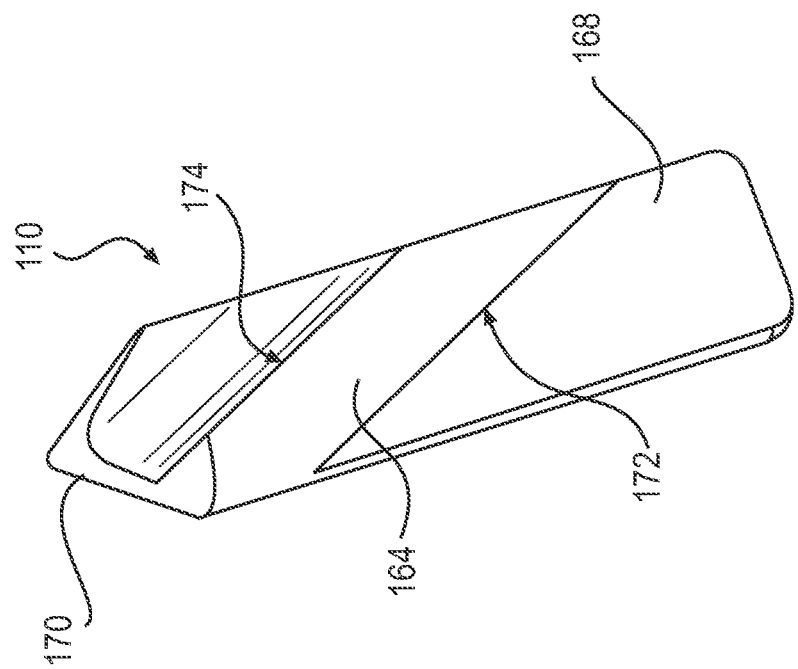

Turning now to FIG. 8, an example body tissue engaging projection 110 is illustrated in more detail in accordance with embodiments of the present disclosure. In the illustrated embodiment, body tissue engaging projection 110 may comprise an elongated body portion 168 and ridge 164. Tissue engaging end 170 may be disposed at one end of elongated body portion 168. While tissue engaging end 170 is show in the form of a conical spike, it should be understood that different shaped tissue engaging ends 170 may be used, including pyramid shaped ends and other pointed protrusions. In operation, the tissue engaging end 170 may engage an adjacent tissue (e.g., vertebral body) to stabilize the spacer 100. As illustrated, ridge 164 may project from elongated body portion 168 and extend at an angle with respect to the elongated body portion 168. As previously described, ridge 164 may ride in cam slots 162 of cam frame 116. Ridge 164 may include a drive surface 172 and a return surface 174. Motion of cam frame 116 may be transferred to body tissue engaging projection 110 through drive surface 172 as body tissue engaging projection 110 is being deployed, while motion of cam frame 116 may be transferred to tissue engaging projection through return surface 174. FIG. 9 illustrates an alternative embodiment of a tissue engaging projection in which drive surface 172 is disposed on an opposite side of ridge 164 from the embodiment shown on FIG. 8. The positioning of drive surface 172 with respect to return surface 174 may depend on the angle of the cam slot 162 into which the body tissue engaging projection 110 may be disposed. Depending on the angle of cam slots 162, the tissue engaging projections 110 of FIGS. 8 and 9 may be use separately or in combination.

Figure 10:
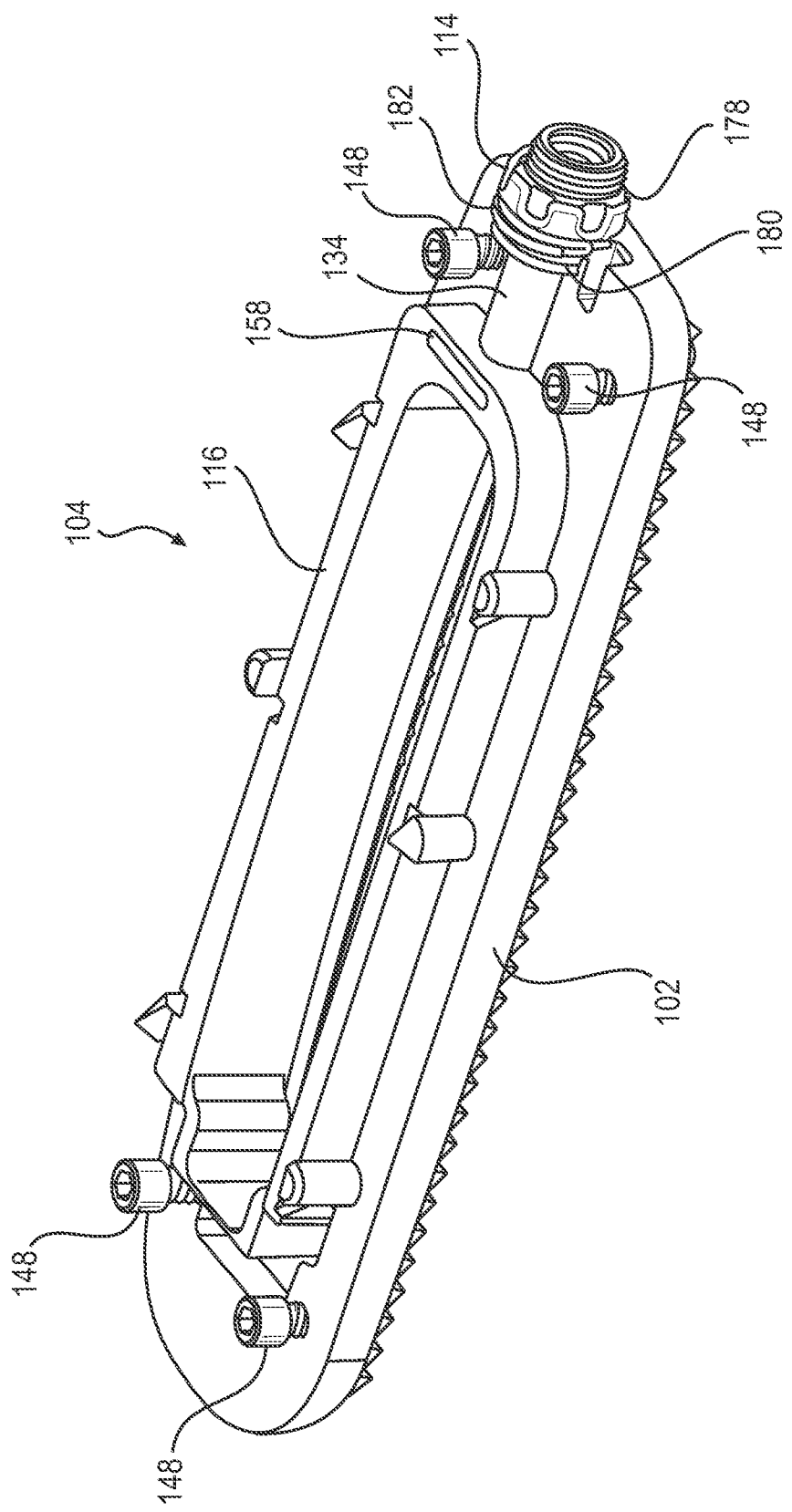
FIGS. 10 and 11 illustrate an actuation subassembly positioned with an endplate in accordance with example embodiments.
Figure 11:
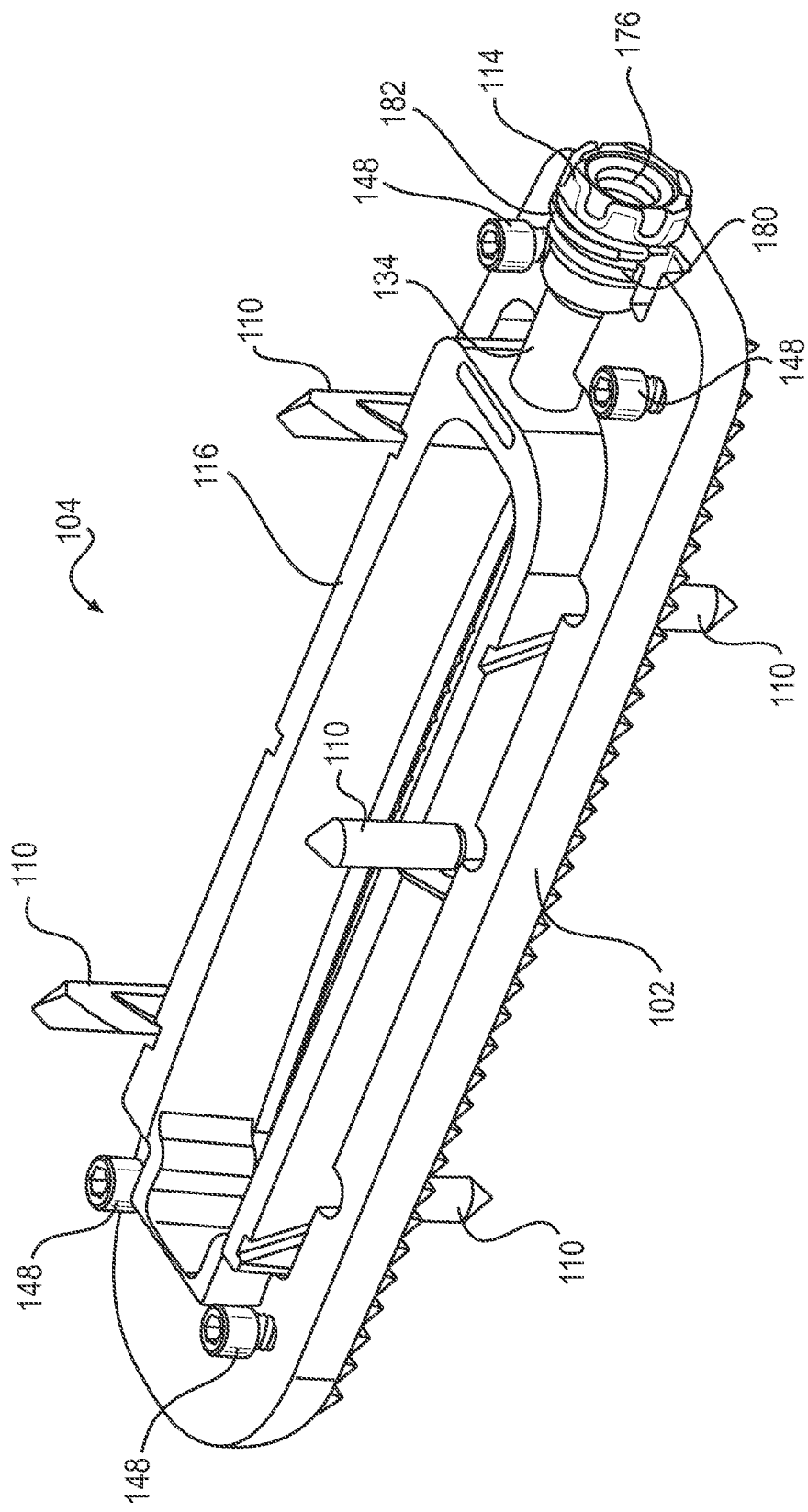

FIGS. 10 and 11 illustrate actuation subassembly 104 in accordance with embodiments of the present invention. Embodiments of actuation subassembly 104 will also described with additional reference to FIG. 5. Action subassembly 104 may extend between endplates 102. In the illustrated embodiments, one of the endplates 102 has been removed to better show actuation subassembly 104. FIG. 10 illustrates the body tissue engaging projections 110 in a retracted position, and FIG. 11 illustrates the body tissue engaging projections 110 in a deployed position.

As illustrated, actuation subassembly 104 may comprise cam frame 116, drive screw 134, and drive nut 114. Cam frame 116 may be displaced relative to endplates 102 by rotation of drive nut 114 which in turn moves drive screw 134 and cam frame 116 along spacer longitudinal axis 112. In some embodiments, rotation of drive nut 114 may cause cam frame 116 to translate a path along spacer longitudinal axis 112. A spacer insertion device (e.g., 190 on FIGS. 12a and 12b) may interact with drive nut 114 to cause rotation of drive nut 114 so that cam frame 116 may be advanced and/or withdrawn. As the cam frame 116 is advanced, the cam frame 116 may drive the body tissue engaging projections 110 from a retracted position (e.g., shown on FIG. 10) to a deployed position (e.g., shown on FIG. 11).

Embodiments of drive nut 114 may also include a nut through bore 176, which may be threaded as best seen on FIG. 5. Drive screw 134 may include a threaded portion 178. Threaded portion 178 may threadingly engage nut through bore 176 so that drive nut 114 may be retained on drive screw 134. While embodiments show drive nut 114 and drive screw 134 as separate components, embodiments may include drive nut 114 integral to, or otherwise formed with, drive screw 134. Embodiments may further include a first ring 180 and a second ring 182, which one or both may be in the form of a c-ring or other suitable device. In some embodiments, first ring 180 may a washer and second ring 182 may be a c-ring. In some embodiments, first ring 180 and/or second ring 182 may be compressible. In some embodiments, first ring 180 and/or second ring 182 may be retained on corresponding grooves found on extension 184 from head portion 186 of drive nut 114. When assembled, first ring 180 may be disposed between endplates 102 and drive nut 114. Second ring 182 may be disposed on extension 184 during insertion into cutouts 132 of endplates 102 and then expand, thus securing drive nut 114 to endplates 102.

In some embodiments, drive screw 134 may be secured in drive nut 114 at one end and be secured to cam frame 116 at another end. Drive screw 134 may include a retainer groove 188. As illustrated, retainer groove 188 may be disposed at an opposite end of drive screw 134 from threaded portion 178. Drive screw 134 may extend into opening 156 in cam frame 116. One or more screw retaining plates 160 may inserted into retaining slots 158 to engage drive screw 134. For example, screw retaining plates 160 may engage retainer groove 188 so that drive screw 134 may be retained in opening 156.

Figure 12A:
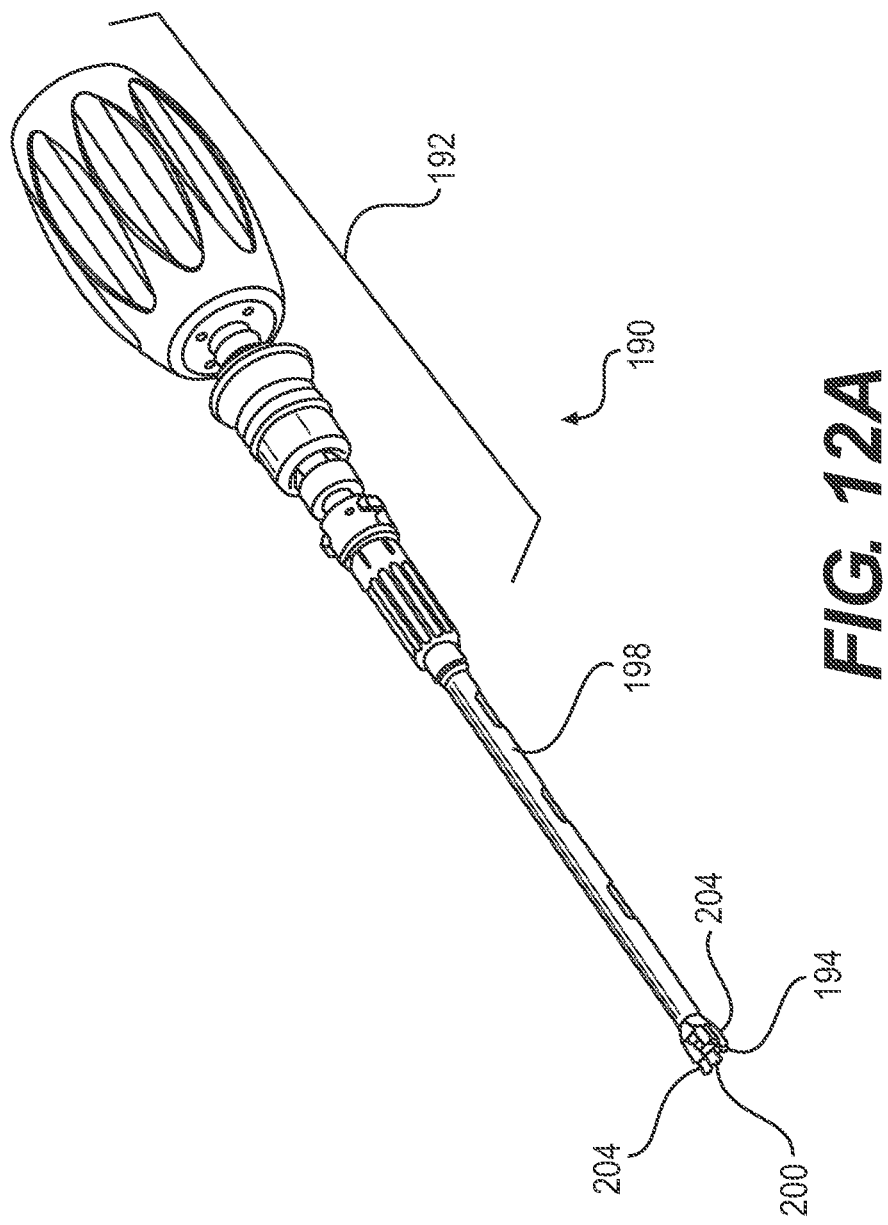
FIGS. 12a and 12b illustrate a spacer insertion device in accordance with example embodiments.
Figure 12B:
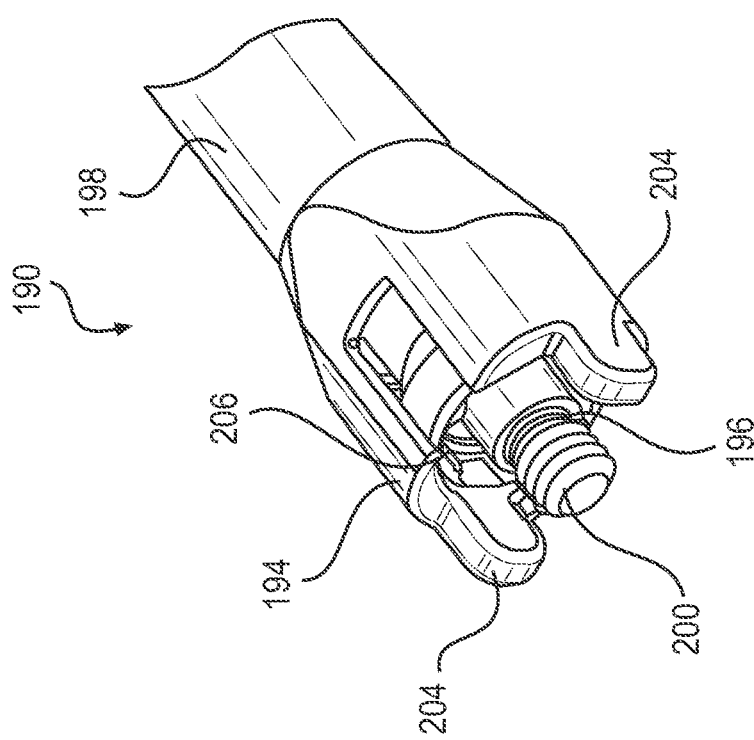

FIGS. 12a and 12b illustrate spacer insertion device 190 in accordance with embodiments of the present invention. Spacer insertion device 190 may be used to engage spacer 100 during its insertion into a patient and also to actuate spacer 100 after its insertion. As illustrated, spacer insertion device 190 may comprise a handle portion 192 and an implant holder portion 194. Spacer insertion device 190 may further comprise an inner shaft 196 and an outer shaft 198. As best seen on FIG. 12b, inner shaft 198 may include a threaded end 200 onto which the spacer 100 may be threaded. For example, threaded end 200 may thread into a threaded opening 202 of drive screw 134 (e.g., shown on FIG. 5). Implant holder portion 194 may also include ears 204 (or other projections) that engage corresponding insertion tool engagements 136 (e.g., shown on FIG. 6a) of endplates 102. Implant holder portion 194 may also include drive nut interface 206 (best seen on FIG. 12b) that engages drive nut 114 to cause rotation of drive nut 114.

Figure 13:
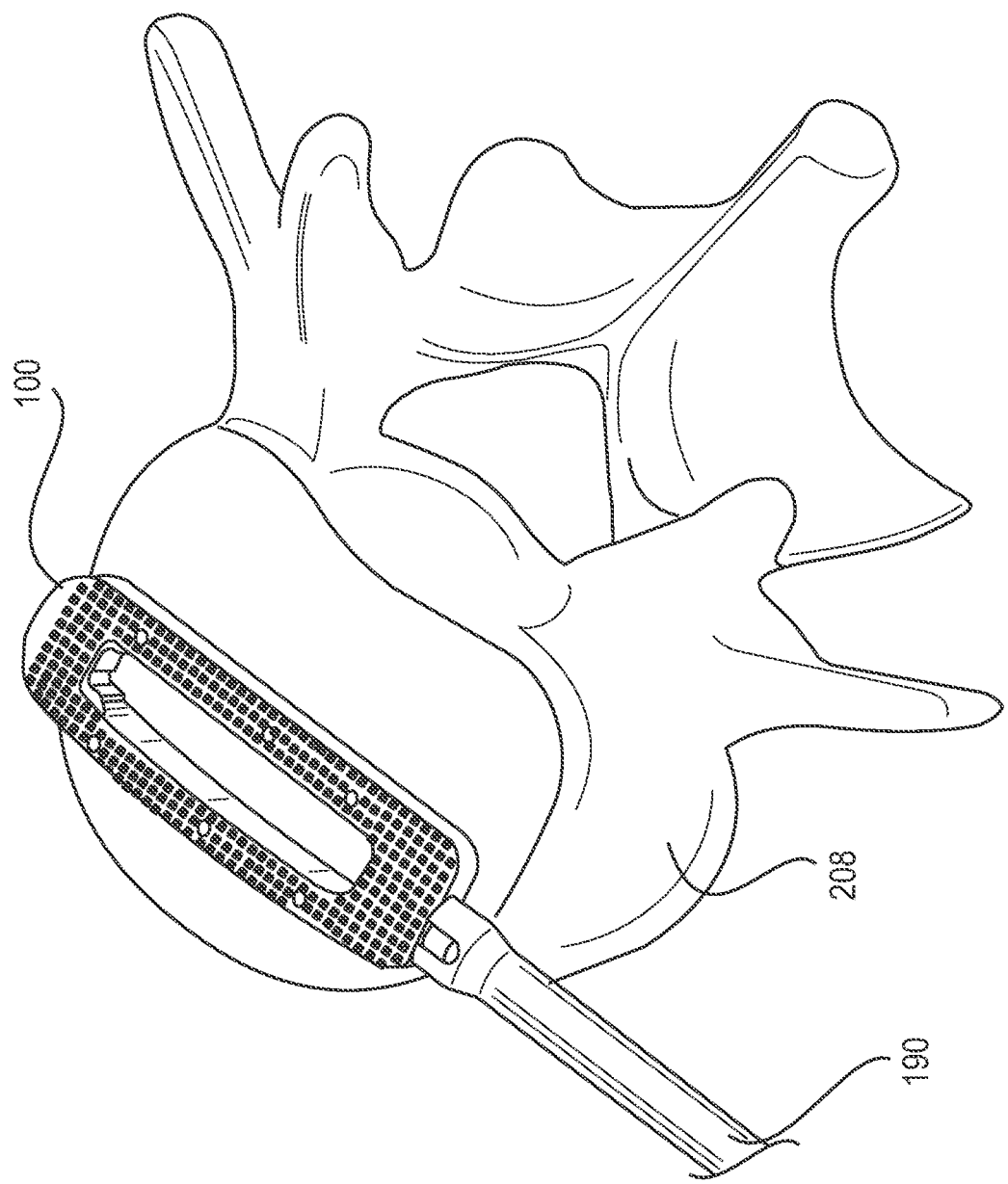
FIG. 13 illustrates insertion of a spacer into a vertebral space in accordance with example embodiments.
Figure 14:
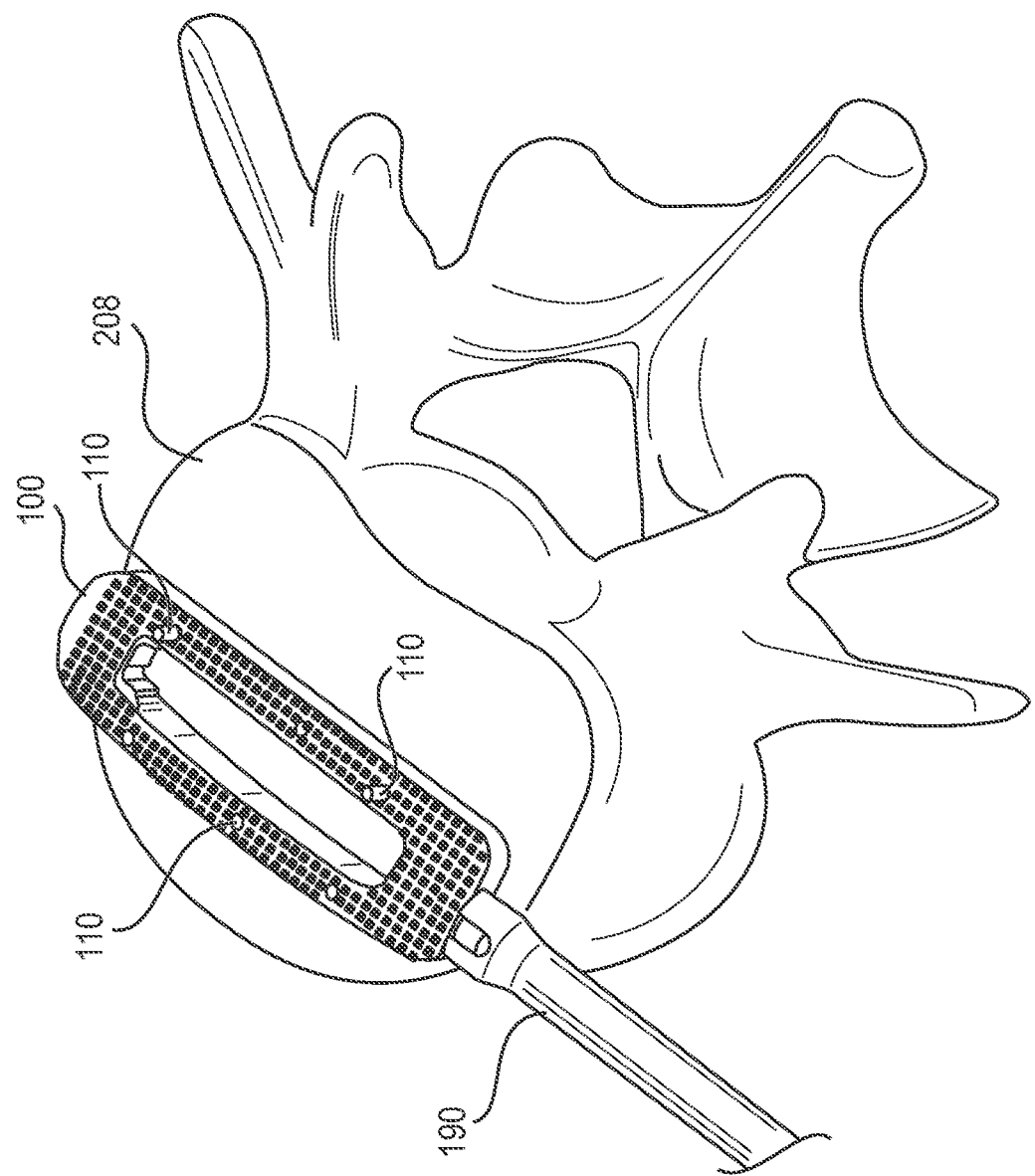
FIG. 14 illustrates deployment of body tissue engaging projections in accordance with example embodiments.
Figure 15:
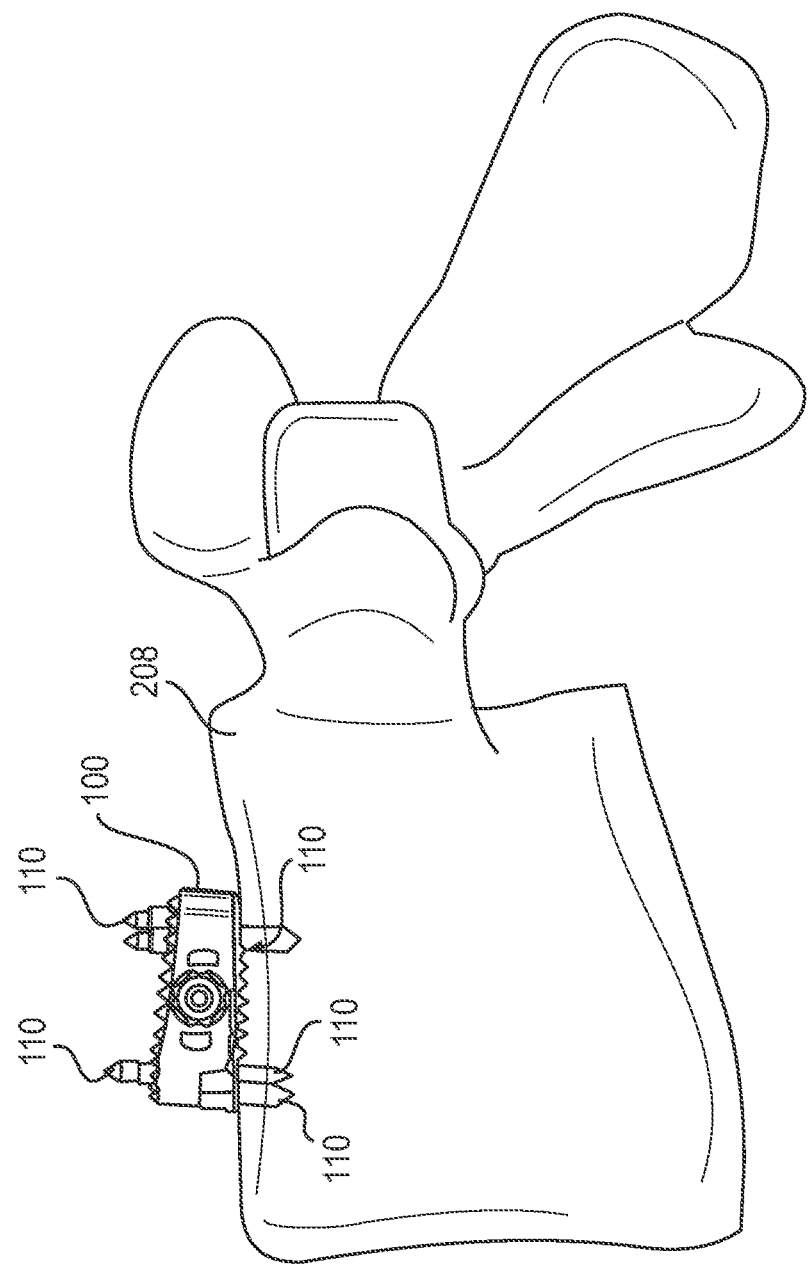
FIG. 15 illustrates a spacer positioned in the vertebral space with body tissue engaging projections being deployed.
Figure 16:
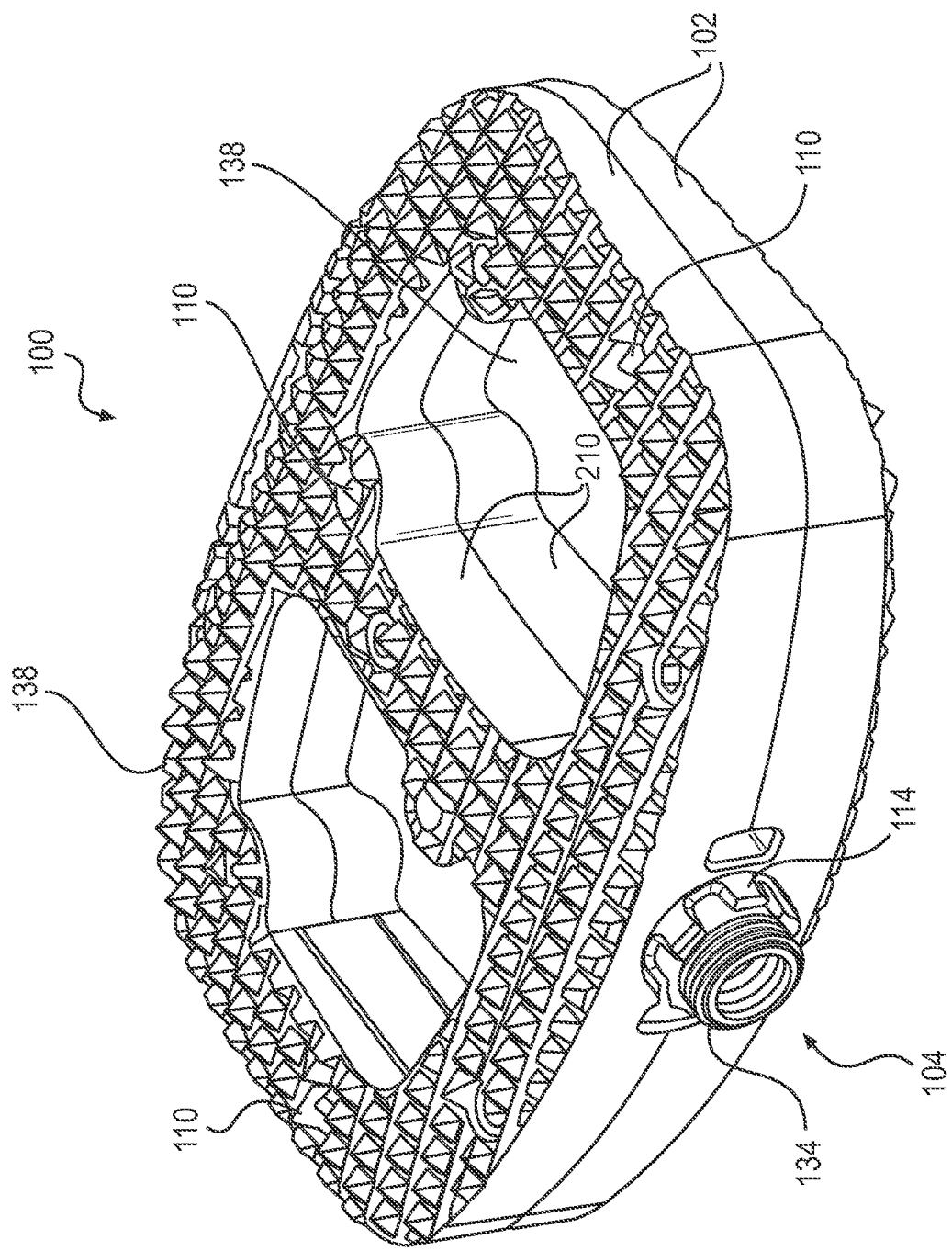
FIG. 16 illustrates a perspective view of a spacer in a retracted position in accordance with example embodiments.
Figure 17:
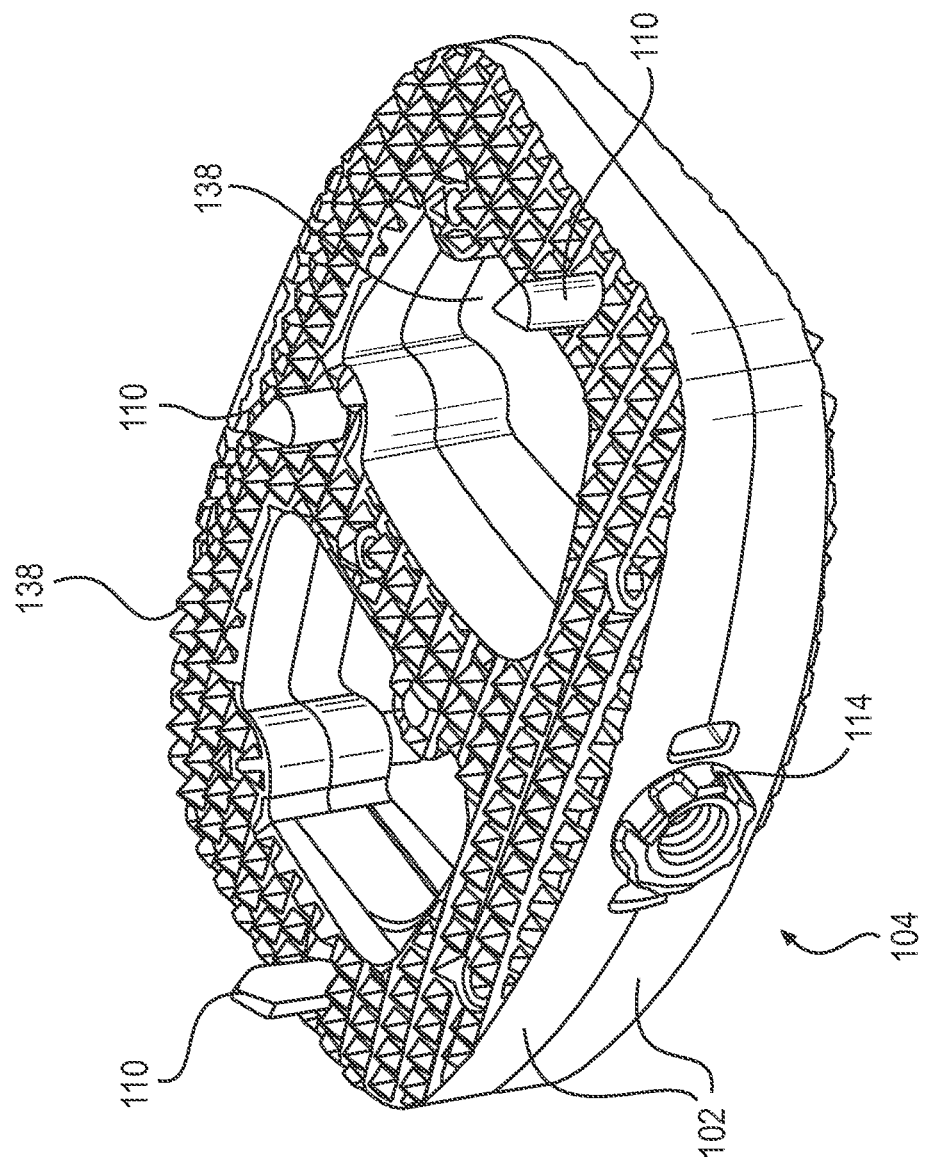
FIG. 17 a perspective view of a spacer with body tissue engaging projections deployed in accordance with example embodiments.
Figure 18:
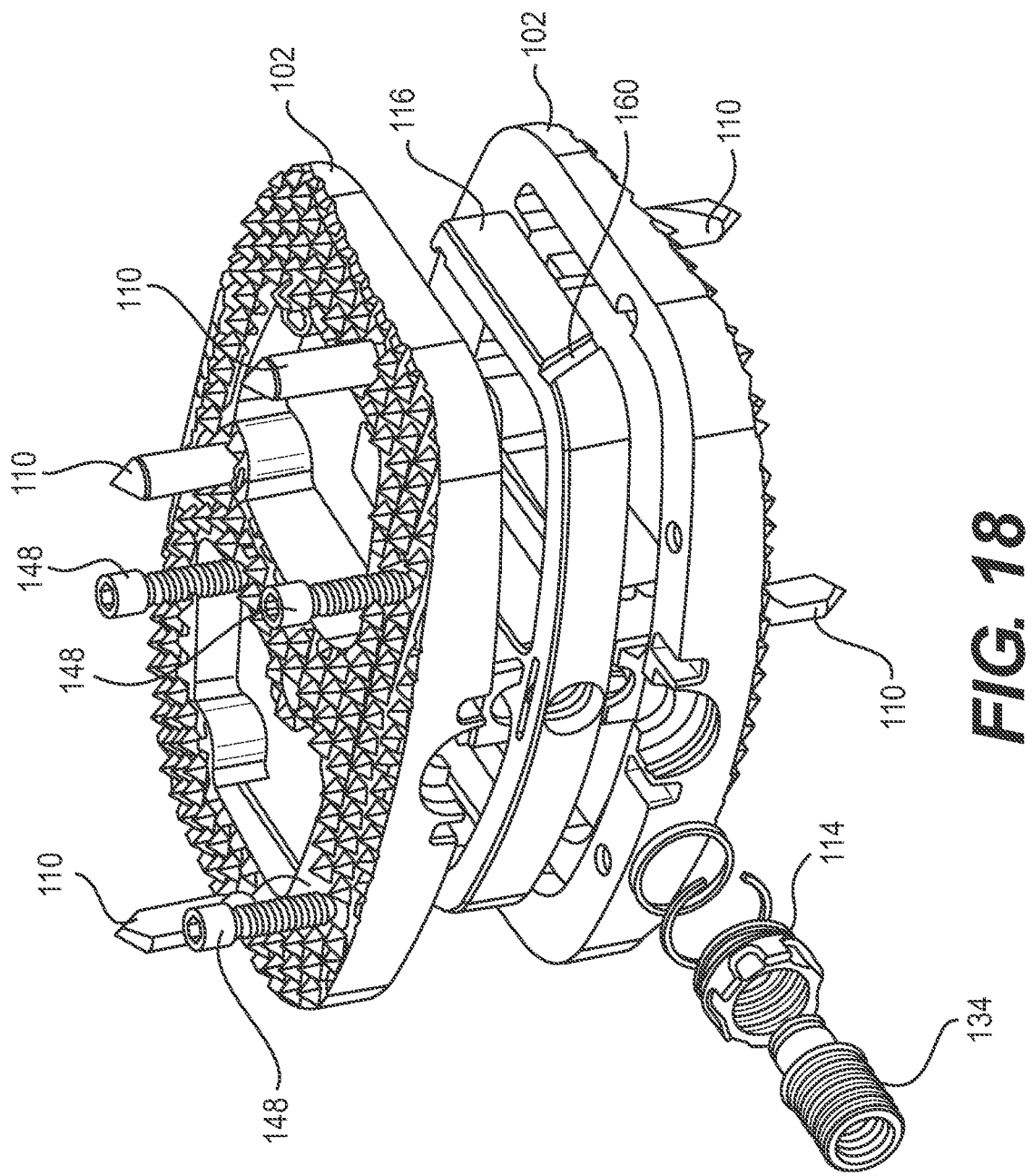
FIG. 18 is an exploded view of a spacer in accordance with example embodiments.
Figure 19:
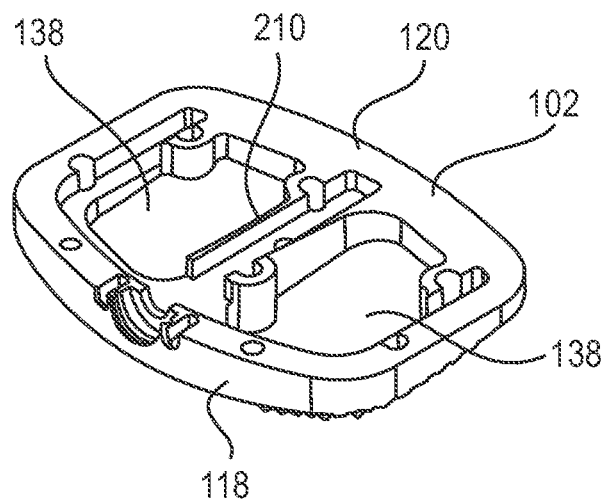
FIG. 19 illustrates an endplate in accordance with example embodiments.
Figure 20:
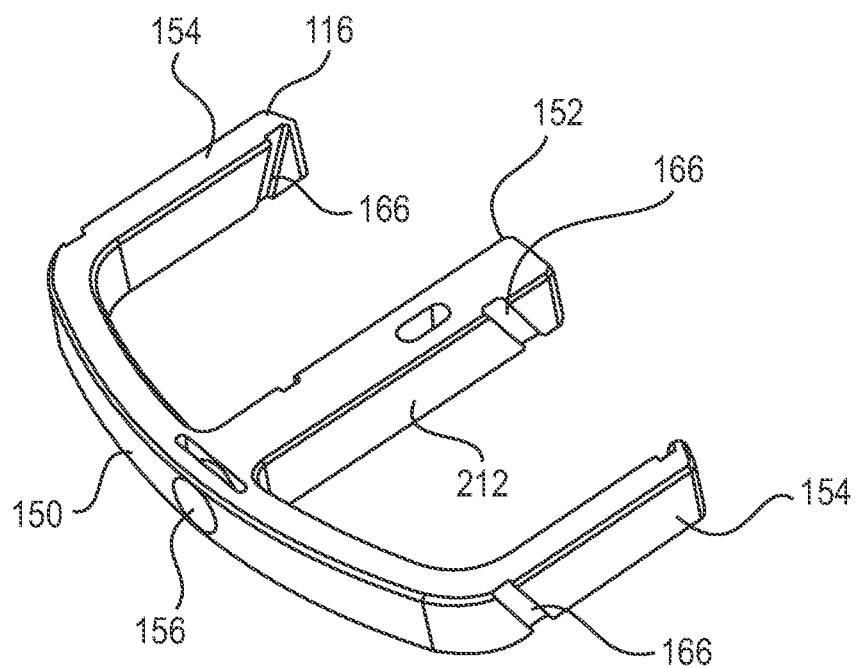
FIG. 20 illustrates a cam frame in accordance with example embodiments.
Figure 21:
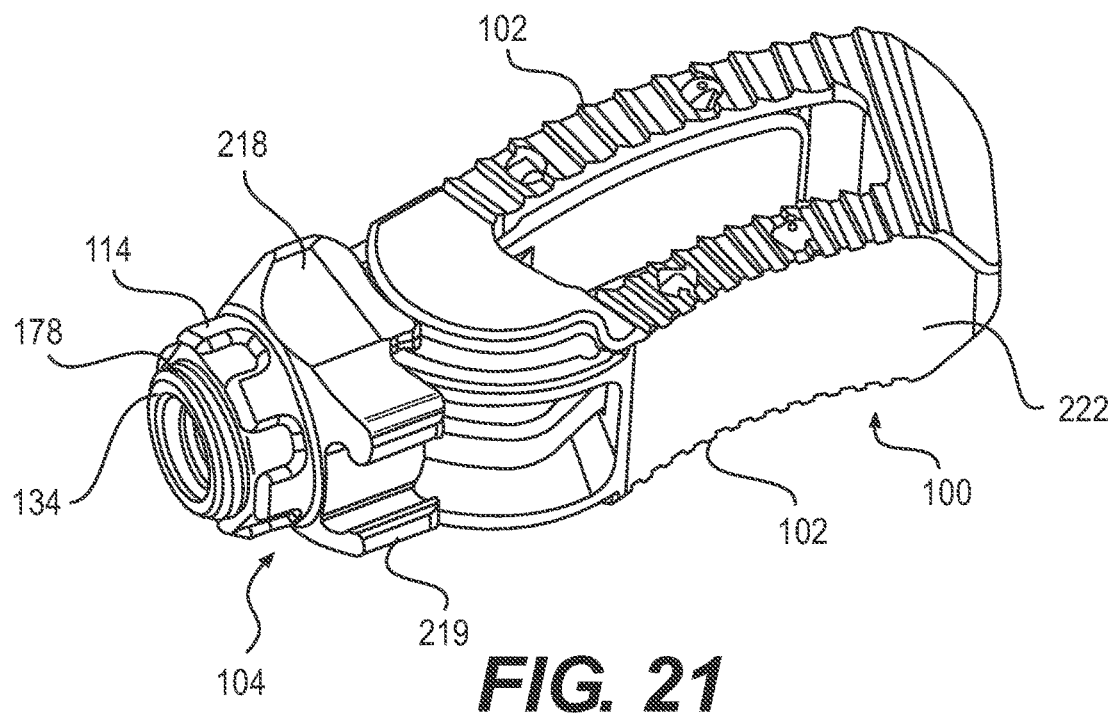
FIG. 21 illustrates a perspective view a spacer with body tissue engaging projections in a retracted position in accordance with example embodiments.
Figure 22:
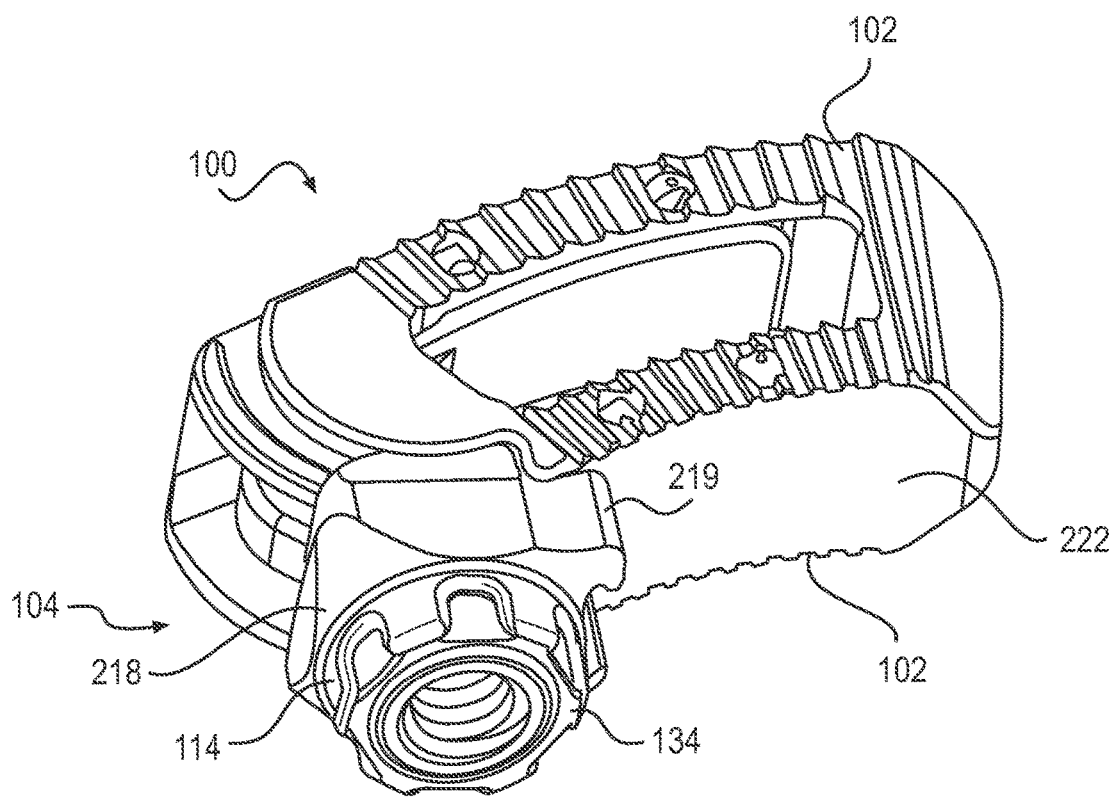
FIG. 22 illustrates a perspective view of a spacer with the drive screw disposed at an angle with respect to the spacer body in accordance example embodiments.

Referring now to FIGS. 13-15, operation of spacer 100 will now be described in accordance with example embodiments. In operation, spacer 100 may be secured to an implant insertion device 190, as shown on FIG. 13. With continued reference to FIG. 13, spacer 100 may be inserted between vertebral bodies 208. For clarity, only one of the vertebral bodies 208 is shown on FIG. 13. Spacer 100 may be inserted between vertebral bodies 208 with body tissue engaging projections 110 in a retracted position. The spacer 100 may be implanted through an anterior, anterolateral, posterior, posterolateral, lateral, or any other approach. The spacer 100 shown on FIGS. 1-11 may be particularly suitable for a lateral approach. After insertion, implant insertion device 190 may be used to rotate drive nut 114 (e.g., shown on FIG. 5) such that body tissue engaging projections 110 may be deployed, as shown on FIG. 14. Implant insertion device 190 may then be detached from spacer 100 and removed from the patient, leaving the spacer 100 in the patient with body tissue engaging projections 110 deployed, as shown on FIG. 15.

Referring now to FIGS. 16-20, in an alternative embodiment, in which like numbers correspond to like elements in other embodiments herein, a spacer 100 is illustrated. As illustrated, the spacer 100 may comprise endplates 102 and actuation subassembly 104. Endplates 102 may be secured to one another by fasteners 148. Actuation subassembly may comprise drive nut 114, drive screw 134, and cam frame 116. Rotation of drive nut 114 may in turn cause drive screw 134 and/or cam frame 116 to advance and/or withdraw. A spacer insertion device (e.g., 190 on FIGS. 12a and 12b) may interact with drive nut 114 for rotation. As the cam frame 116 is advanced, the cam frame 116 may drive the body tissue engaging projections 110 from a retracted position (e.g., shown on FIG. 16) to a deployed position (e.g., shown on FIG. 17).

Embodiments of spacer 100 shown on FIGS. 16-20 may be generally similar in function and operation to the embodiments of spacer 100 shown on FIGS. 1-11, except that spacer 100 may have a different configuration. By way of example, instead of one through opening 138 in endplates 102, each endplate 102 may comprise a pair of through openings 138. In addition, endplates 102 may also comprise a central extension 210 that extends from proximal end 118 to distal end 120. Additionally, cam frame 116 may be open at one end, for example, the distal frame end 152, which may be opposite opening 156, as best seen on FIG. 20. Moreover, a central frame extension 212 may extend from proximal frame end 150 between lateral frame sides 154. While the spacer 100 shown on FIGS. 16-20 may be inserted using a variety of approaches, it may be particularly suitable for an anterior or anterolateral approach.

Figure 23:
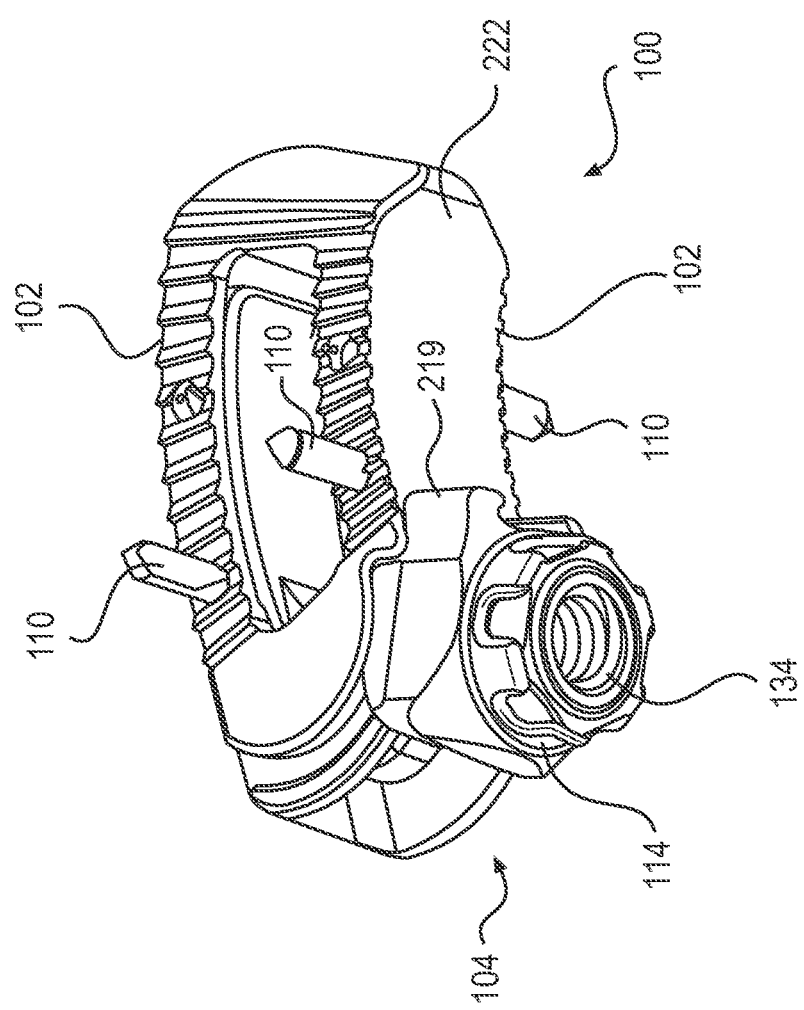
FIG. 23 illustrates a perspective view of a spacer with the drive screw disposed at an angle with respect to the spacer body and the body tissue engaging projections in a deployed position in accordance example embodiments.
Figure 24:
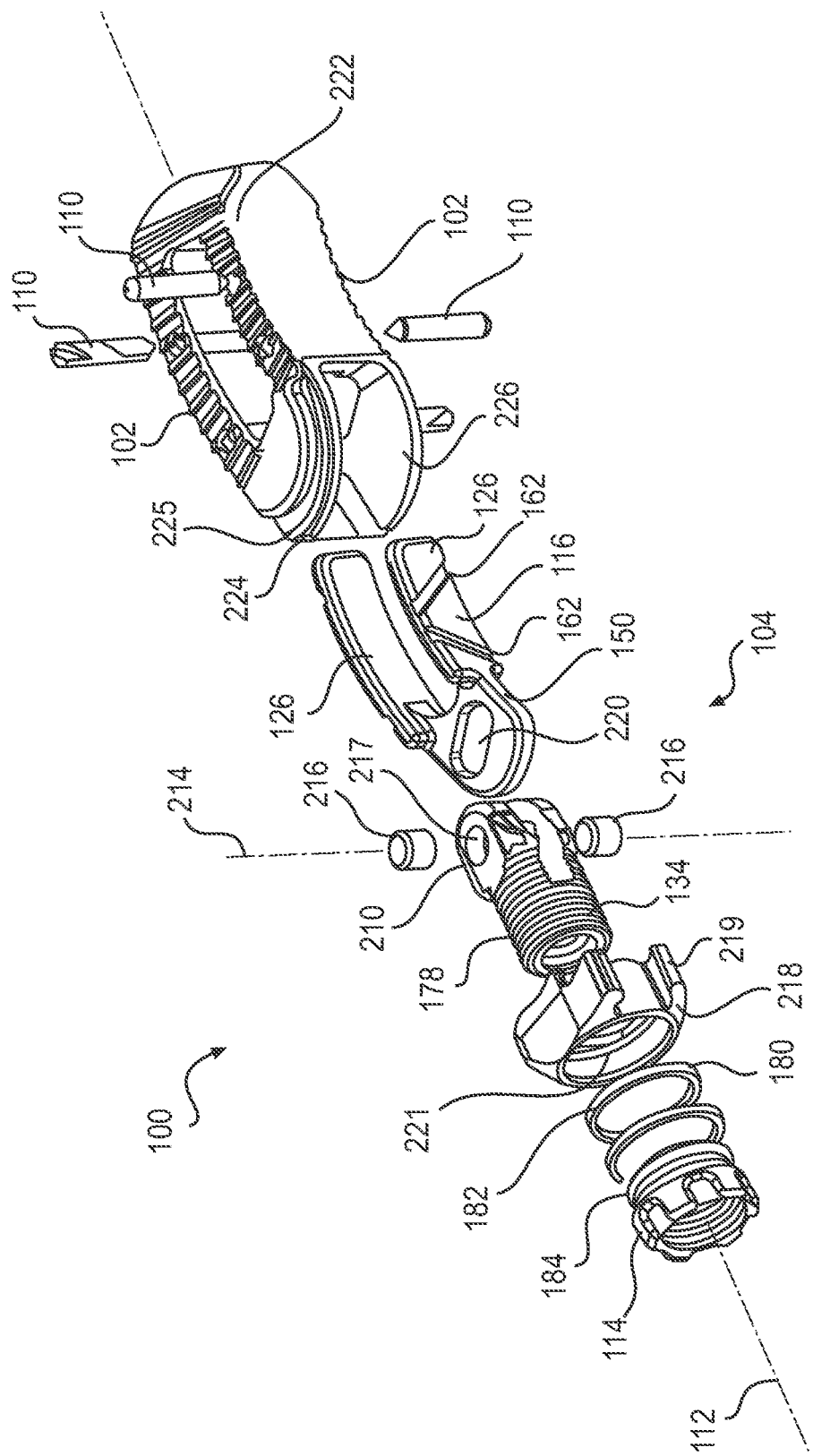
FIG. 24 is an exploded view of a spacer in accordance with example embodiments.
Figure 25:
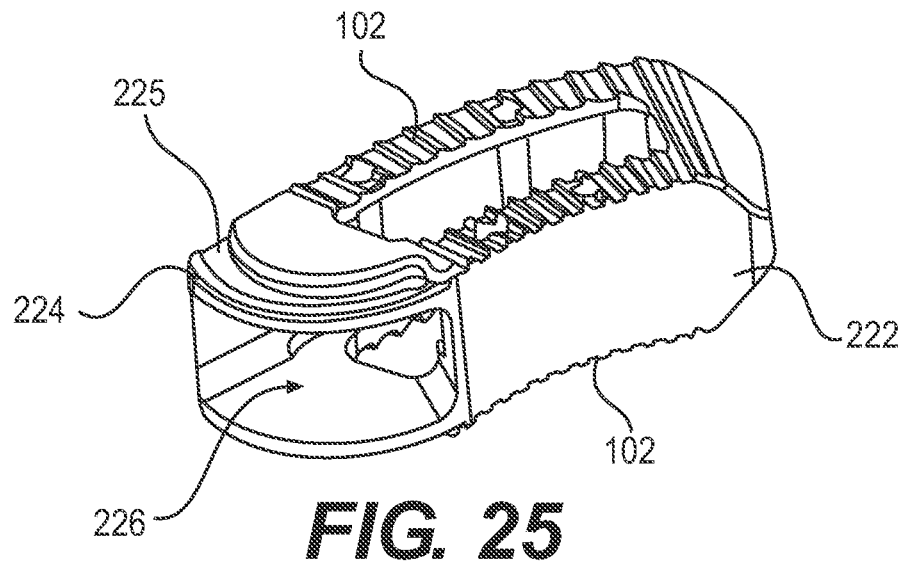
FIG. 25 illustrates a spacer body in accordance with example embodiments.
Figure 26:
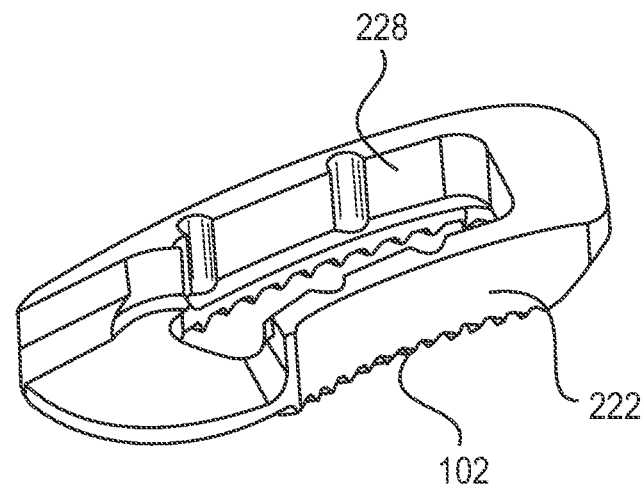
FIG. 26 is a cut away view of a spacer body in accordance with example embodiments.
Figure 27:
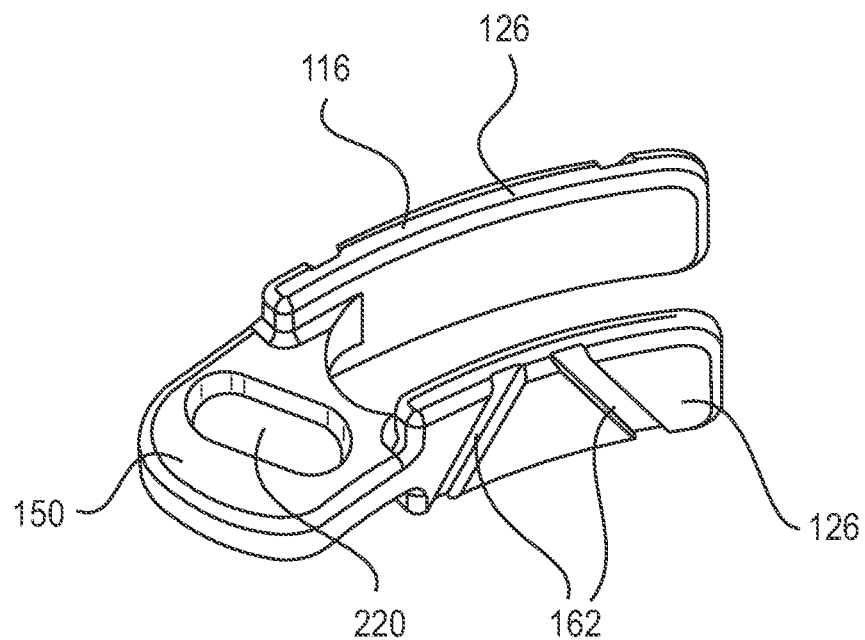
FIG. 27 illustrates a cam frame in accordance with example embodiments.

Referring now to FIGS. 21-27, in an alternative embodiment, in which like numbers correspond to like elements in other embodiments herein, a spacer 100 is illustrated. As illustrated, the spacer 100 may comprise endplates 102 and actuation subassembly 104. Actuation subassembly 104 may comprise drive nut 114, drive screw 134, and cam frame 116. Spacer 100 may be inserted in a retracted position, as shown on FIG. 21. In the retracted position, body tissue engaging projections 110 (best seen on FIGS. 23 and 24) are disposed within spacer 100 and may not extend beyond endplates 102. In other words, the body tissue engaging projections 110 may be considered to be in a retracted position. After insertion of the spacer 100, cam frame 116 may be pivoted with respect to drive screw 134 to provide a desired orientation of spacer 100, as best seen on FIG. 22. Turning now to FIG. 23, body tissue engaging projections 110 may then be deployed to engage tissue (e.g., endplates), for example, to fixate spacer 100 in place. To deploy body tissue engaging projections 110, drive nut 114 may be rotated causing advancement and/or retraction of cam frame 116 along spacer longitudinal axis 112. As the cam frame 116 (best seen on FIG. 5) is moved, it engages body tissue engaging projections 110 driving them outward such that the body tissue engaging projections 110 are deployed through the endplates 102.

In some embodiments, drive screw 134 may comprise a threaded portion 178 at one end and a clevis portion 212 at another end. Threaded portion 178 may secure drive screw 134 to drive nut 114. Cam frame 116 may comprise lateral sides 126 in which cam slots 162 may be formed. Drive screw 134 may be pivotally engaged with cam frame 116 to pivot about a vertical axis 214, substantially perpendicular to spacer longitudinal axis 112. Pin 216 may pass through openings 217 in clevis portion and pass through slot 220 in proximal frame end 150 to secure drive screw 134 to cam frame 116. In some embodiments, drive screw 134 may pivot about pin 216. In the embodiment shown in FIG. 24, pin 216 may be segmented but alternative embodiments may include use of a unitary pin. Similarly, regardless of a given orientation of drive screw 134 with respect to cam frame 116, rotation of drive nut 114 advances or withdraws drive screw 134, causing movement of cam frame 116 relative to endplates 102.

In some embodiments, actuation subassembly 104 may further comprise a pivot housing 218. Drive nut 114 may be coupled to pivot housing 218. For example, first ring 180, such as a washer, and second ring 182, such as a c-ring, may be retained on extension 184 of drive nut 114. First ring 180 and second ring 182 may also interact with corresponding grooves in through bore 221 of pivot housing 218 to retain drive nut 114 thereto. Pivot housing 218 may include a tool engagement 219, which may be a slot or otherwise formed. Tool engagement 219 may engage a corresponding engagement of spacer insertion device (e.g., 190 on FIG. 28).

In some embodiments, spacer 100 may further comprise a spacer body 222. As best seen on FIG. 25, endplates 102 may be formed on opposite sides of spacer body 222. In some embodiments, endplates 102 may be integral to spacer body 222. However, embodiments may include endplates 102 that are separately formed and attached to spacer body 222. Proximal body end 224 may include an opening 226 that receives actuation subassembly 104. Outer facing surface 124 of spacer body 222 may include a pivot housing groove 225 at proximal body end 224. Pivot housing groove 225 may retain pivot housing 218 and form a track in which pivot housing 218 rides. As best seen in the cut-away view of FIG. 26, spacer body 222 may also include a central opening 228 in which cam frame 116 may be disposed.

Figure 28:
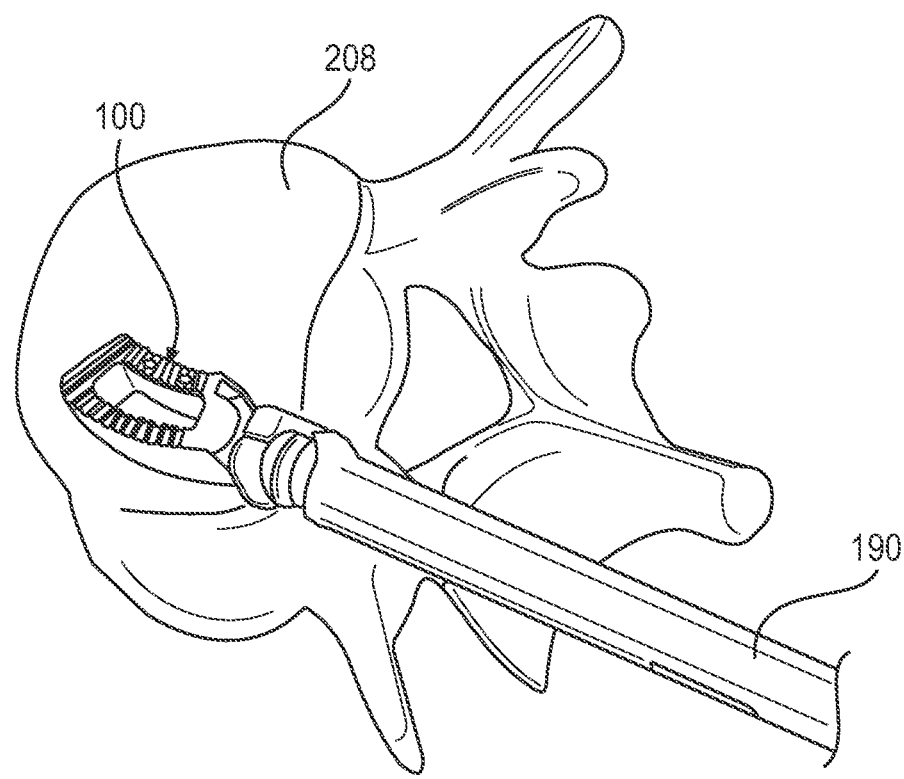
FIG. 28 illustrates insertion of a spacer into a vertebral space in accordance with example embodiments.
Figure 29:
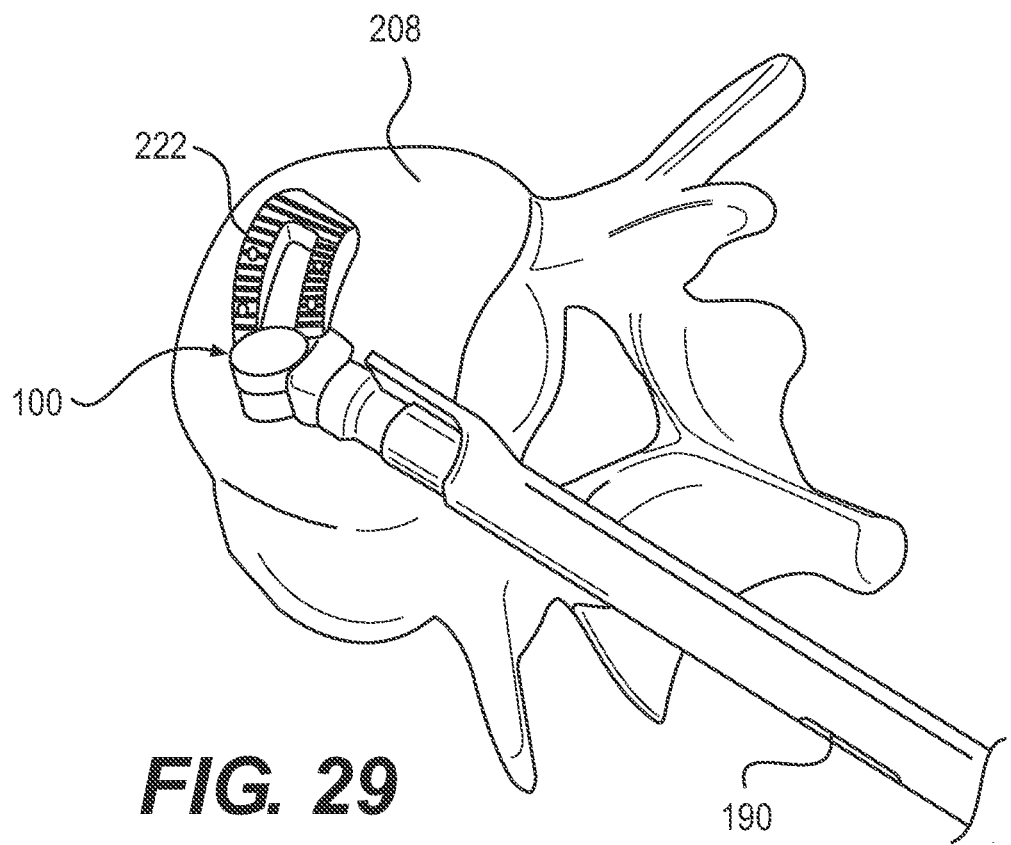
FIG. 29 illustrations articulation of a spacer body after insertion of the spacer in the vertebral space in accordance with example embodiments.
Figure 30:
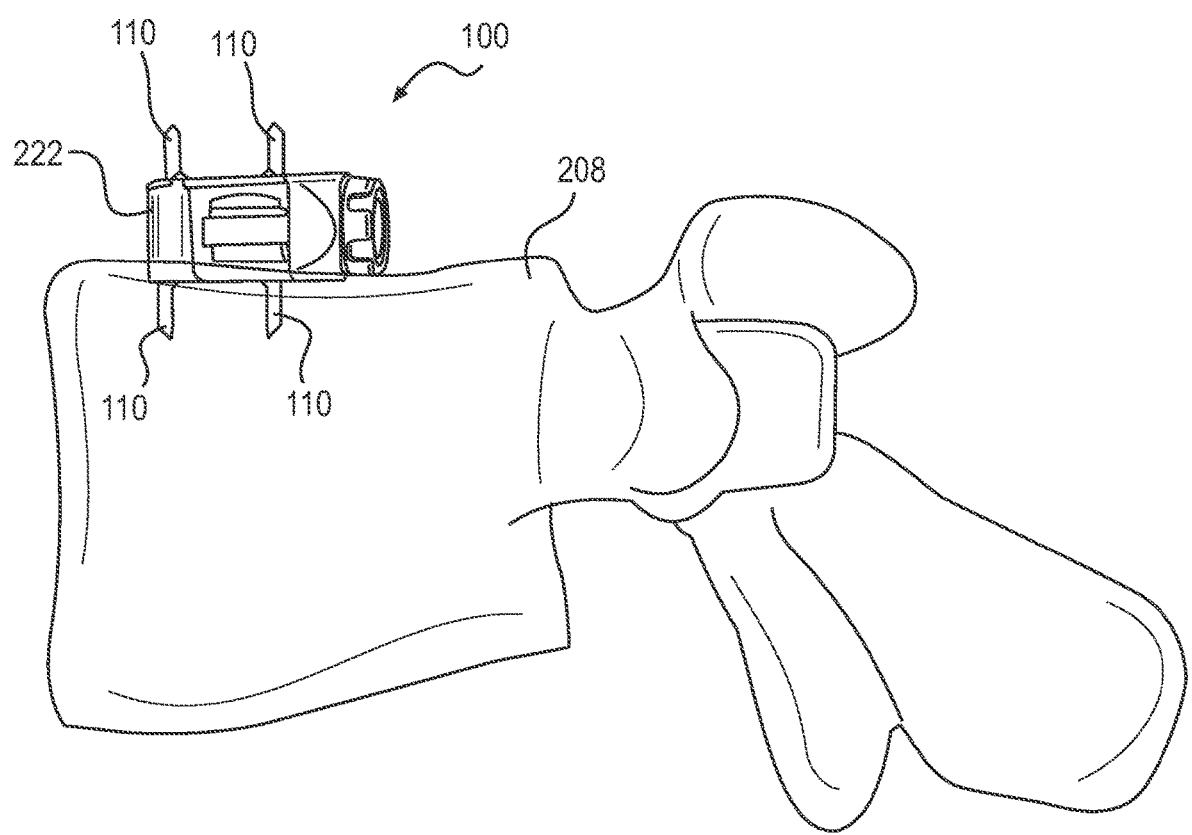
FIG. 30 illustrates a spacer positioned in the vertebral space in an articulated position with body tissue engaging projections being deployed.

Referring now to FIGS. 28-30, operation of spacer 100 will now be described in accordance with example embodiments. In operation, spacer 100 may be secured to an implant insertion device 190, as shown on FIG. 28. With continued reference to FIG. 28, spacer 100 may be inserted between vertebral bodies 208. For clarity, only one of the vertebral bodies 208 is shown on FIG. 28. Spacer 100 may be inserted between vertebral bodies 208 with tissue engaging projections 110 in a retracted position. The spacer 100 may be implanted through an anterior, anterolateral, posterior, posterolateral, lateral, or any other approach. The spacer shown on FIGS. 21-27 may be particularly suitable for a posterior or posterolateral approach. After insertion, implant insertion device 190 may be used to pivot cam frame 116 and, in turn, spacer body 222 about drive screw 134 (e.g., shown on FIG. 24). Pivoting of spacer body 222 may be seen on FIG. 29. Thereafter, drive nut 114 (e.g., shown on FIG. 24) may be rotated such that body tissue engaging projections 110 may be deployed. Implant insertion device 190 may then be detached from spacer 100 and removed from the patient, leaving the spacer 100 in the patient with body tissue engaging projections 110 deployed, as shown on FIG. 30.

In some embodiments, spacer 100 may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; stainless steel, polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material. Portions or all of the spacer 100 may be radiopaque or radiolucent, or materials having such properties may be added or incorporated into the spacer 100 to improve imaging of the device during and after implantation. Any surface or component of a spacer 100 may be coated with or impregnated with therapeutic agents, including bone growth, healing, antimicrobial, or drug materials, which may be released at a therapeutic rate, using methods known to those skilled in the art.

In some embodiments, spacer 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of spacers 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the disclosed spacers 100. For example, polymeric portions can be formed with PEEK-OPTIMA, which is radiolucent, whereby bony ingrowth may be observed. Other polymeric materials with suitable flexibility, durability, and biocompatibility may also be used.

In accordance with present embodiments, spacer 100 may be provided in various sizes to best fit the anatomy of the patient. Components of matching or divergent sizes may be assembled during the implantation procedure by a medical practitioner as best meets the therapeutic needs of the patient, the assembly inserted within the body using an insertion tool. In some embodiments, spacer 100 may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

In some embodiments, a single spacer 100 may be used, to provide stabilization for a weakened joint or joint portion. Alternatively, a combination of two, three, or more of any of spacer 100 may be used, at a single joint level, or in multiple joints. Moreover, implants of the disclosure may be combined with other stabilizing means.

In some embodiments, a spacer 100 may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

In some embodiments, a spacer 100 may be provided to be support adjacent vertebrae during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). The surgery to implant spacer 100 may be performed through an Anterior, Anterolateral, Posterolateral, Lateral, or any other approach.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Although the present invention and its advantages have been described in detail, it should be understood that various changes, substitutions and alterations may be made herein without departing from the spirit and scope of the invention as defined by the appended claims.

What is claimed is:

1. A spacer for separating bones of a joint, the spacer comprising:
   a first endplate configured to engage a first bone of the joint;
   a second endplate configured to engage a second bone of the joint;
   tissue engaging projections, wherein the tissue engaging projections each comprise an elongated body portion and a ridge that extends at angle with respect to the elongated body; and
   an actuation subassembly that extends between the first endplate and the second endplate,
   wherein the actuation subassembly further includes a cam frame comprising a proximal frame end, a distal frame end, and lateral frame sides.

2. The spacer of claim 1, wherein the actuation subassembly includes a drive nut comprising a head portion and an extension from the head portion, wherein the extension is secured in a cutout formed in each of the first endplate and the second endplate.

3. The spacer of claim 2, wherein the actuation subassembly further includes a drive screw comprising a threaded end that is threadingly coupled to a through bore of the drive nut.

4. The spacer of claim 3, wherein cam slots that engage the tissue engaging projections are formed in the lateral frame sides of the actuation subassembly.

5. The spacer of claim 4, wherein the cam slots are at an angle with respect to a longitudinal axis of the spacer.

6. The spacer of claim 5, wherein the drive screw is retained in an opening in the proximal frame end.

7. The spacer of claim 1, wherein the elongated body portion includes a tissue engaging end.

8. The spacer of claim 7, wherein the tissue engaging projections are moveable from a retracted position to a deployed position.

9. The spacer of claim 8, wherein the actuation subassembly is configured to engage the tissue engaging projections.

10. A spacer for separating bones of a joint, the spacer comprising:
    a first endplate configured to engage a first bone of the joint;
    a second endplate configured to engage a second bone of the joint;
    tissue engaging projections, wherein the tissue engaging projections are moveable from a retracted position to a deployed position; and
    an actuation subassembly configured to deploy and retract the tissue engaging projections,
    wherein the actuation subassembly further includes a cam frame comprising a proximal frame end, a distal frame end, and lateral frame sides.

11. The spacer of claim 10, wherein the actuation subassembly includes a drive nut comprising a head portion and an extension from the head portion, wherein the extension is secured in a cutout formed in each of the first endplate and the second endplate.

12. The spacer of claim 11, wherein the actuation subassembly further includes a drive screw comprising a threaded end that is threadingly coupled to a through bore of the drive nut.

13. The spacer of claim 12, wherein cam slots that engage the tissue engaging projections are formed in the lateral frame sides of the actuation subassembly.

14. The spacer of claim 13, wherein the cam slots are at an angle with respect to a longitudinal axis of the spacer.

15. The spacer of claim 14, wherein the drive screw is retained in an opening in the proximal frame end.

16. The spacer of claim 10, wherein the elongated body portion includes a tissue engaging end.

17. The spacer of claim 16, wherein the tissue engaging projections are moveable from a retracted position to a deployed position.

18. The spacer of claim 17, wherein the actuation subassembly is configured to engage the tissue engaging projections.

* * * * *